United States Patent [19]

Rubinsky et al.

[11] Patent Number: 5,358,931
[45] Date of Patent: Oct. 25, 1994

[54] INTERACTION OF THERMAL HYSTERESIS PROTEINS WITH CELLS AND CELL MEMBRANES AND ASSOCIATED APPLICATIONS

[75] Inventors: Boris Rubinsky, Albany, Calif.; Arthur L. Devries, Urbana, Ill.; Amir Arav, Albany, Calif.

[73] Assignee: The Regents of the University of California, Alameda, Calif.

[21] Appl. No.: 4,919

[22] Filed: Jan. 15, 1993

Related U.S. Application Data

[63] Continuation-in-part of Ser. No. 910,151, Jul. 16, 1992, abandoned, Ser. No. 910,254, Jul. 16, 1992, abandoned, and Ser. No. 562,461, Aug. 3, 1990, abandoned, which is a continuation-in-part of Ser. No. 466,050, Jan. 17, 1990, abandoned.

[51] Int. Cl.⁵ ............... A61K 37/00; A61K 37/10; A01N 1/02
[52] U.S. Cl. ........................... 514/12; 514/21; 514/2; 514/8; 435/1; 424/523
[58] Field of Search ............ 514/12, 21, 8; 435/1, 435/2; 424/523

[56] References Cited

U.S. PATENT DOCUMENTS

| | | | |
|---|---|---|---|
| 3,817,837 | 6/1974 | Rubenstein | 195/103.5 R |
| 4,059,967 | 11/1977 | Rowe et al. | 62/64 |
| 4,104,466 | 8/1978 | Tsuchida et al. | 542/433 |
| 4,155,331 | 5/1979 | Lawrence et al. | 119/2 |
| 4,186,253 | 1/1980 | Yokoyama et al. | 435/240 |
| 4,531,373 | 7/1981 | Rubinsky | 62/63 |
| 4,663,289 | 5/1987 | Veech | 435/240 |
| 4,688,387 | 8/1987 | Conaway | 62/78 |
| 4,772,681 | 9/1988 | Fukuda et al. | 540/145 |
| 4,931,361 | 6/1990 | Baldeschwieler | 428/402.2 |
| 4,959,319 | 9/1990 | Skelnik et al. | 435/240 |
| 4,980,277 | 12/1990 | Junnila | 435/2 |
| 5,001,047 | 3/1991 | Liberman | 435/1 |
| 5,075,210 | 12/1991 | Wikman-Coffelt | 435/1 |
| 5,160,312 | 3/1992 | Voekel | 600/34 |

FOREIGN PATENT DOCUMENTS 139200 12/1979 Fed. Rep. of Germany.

OTHER PUBLICATIONS

Renzi, F., et al., "Partition Coefficients of Volatile Anesthetics in Kreb's Solution", *Anesthesiology*, vol. 47, pp. 62–63, 1977.

(List continued on next page.)

*Primary Examiner*—Douglas W. Robinson
*Assistant Examiner*—Jon P. Weber
*Attorney, Agent, or Firm*—Townsend and Townsend Khourie and Crew

[57] ABSTRACT

A newly discovered property of thermal hysteresis proteins is the interaction of these proteins with cell membranes and thus with cells themselves, protecting cells and their membranes from damage which they would otherwise suffer upon exposure to non-physiological conditions such as temperature abnormalities, including both hyperthermic, hypothermic and sub-freezing temperatures. Improved rates of cell viability are observed over a wide range of conditions which do not involve ice formation, including temperatures above the freezing range as well as temperatures below the freezing range but in vitrification conditions. Heretofore the only known property of these proteins was their ability to interact with ice crystals. In conditions in which ice crystals are formed, it is further discovered that use of the proteins with human cells at the concentrations in which they naturally occur in the source organisms results in aggravating the injury to the cells rather than reducing it, but that the injury is lessened, and the survival rate improved, by using low concentrations. The proteins thus offer benefits in the preservation and improved viability of cell suspensions, tissues and whole organs. The proteins are further discovered to have the ability to block ion channels in mammalian cell membranes, thereby providing a further utility in the treatment of disease conditions.

38 Claims, No Drawings

OTHER PUBLICATIONS

Krebs, H. A., "Metabolic Requirements of Isolated Organs", *Transplantation Proceeding*, vol. VI, No. 3, pp. 237–239, 1974.

Onik, G., et al., "Cryosurgery: New Developments in Understanding and Technique", Abstract, pp. 57–80.

Rubinsky, B., et al., "Cryopreservation of Oocytes using Directional Cooling and Antifreeze Glycoproteins", Abstract, *Cryo–Letters*, vol. 12, pp. 93–106, (1991).

Chou, P. Y., et al., "Prediction of Protein Conformation", *Biochemistry*, vol. 13, No. 2, pp. 222–245, 1974.

Krebs, H. A., et al., "Untersuchungen über die Harnstoffbildung im Tierkörper", no English Translation, *Zeit Phiol.*, vol. 210, pp. 33–66, 1932.

Rubinsky, B., et al., "A Mathematical model for the freezing proscess in biological tissue", *Proc. R. Soc. Lond.*, vol. B234, pp. 343–358, 1988.

Ewart, K. V., et al., "Structural and Functional Similarity Between Fish Antifreeze Proteins and Calcium-Dependent Lectins", *Biochemical and Biophysical Research Communications*, vol. 185, No. 1, pp. 335–340, 1992.

Rubinsky, B., et al., "The Cryoprotective Effect of Antifreeze Glycopeptides from Antarctic Fishes", *Crybiology*, vol. 29, pp. 69–79, 1992.

Rubinsky, B., et al., "Hypothermic Protection–A Fundamental Property of Antifreeze Proteins", *Biochemical and Biophysical Research Communications*, vol. 180, No. 2, pp. 566–571, 1991.

Rubinsky, B., et al., "Inhibition of $Ca^{2+}$ and $K^+$ currents by Antifreeze proteins", *Am. J. Physiol.*, vol. 262, pp. R542–R545, 1992.

Lee, C. Y., et al., "Hypothermic preservation of whole mammalian organs with 'antifreeze' proteins", *Cryo–Letter*, vol. 13, pp. 59–66, 1992.

Karow, A. M., et al., "Cryopreservation: Pharmacological Considerations", *Organ Preservation for Transplantation*, Chpt. 5, pp. 86–107, 1974.

Pegg, D., "Ice Crystals in Tissues and Organs", *The Biophysics of Organ Cryopreservation*, pp. 117–140, 1987.

Rubinsky, B., et al., "A mathematical model for the freezing process in biological tissue", *Proc. R. Soc. Lond.*, vol. B234, pp. 343–358, 1988.

DeVries, A. L., et al., "The Role of Glycoprotein Antifreezes in the Survival of Antarctic Fishes", *The Proceedings of the Third SCAR Symposium on Antarctic Biology*, pp. 439–458, 1977.

Raymond, J. A., et al., "Spontaneous Emulsification of Oil by Freezing", *Journal of Colloid and Interface Science*, vol. 52, No. 2, 1975.

Ahlgren, J. A., et al., "Freezing Avoidance and the Distribution of Antifreeze Glycopeptides in Body Fluids and Tissues of Antarctic Fish", *J. Exp. Biology*, vol. 137, pp. 549–563, 1988.

Cheng, Chi–Hing C., et al., "Structures of antifreeze peptides from the antarctic eel pout, *Austrolycicthys brachycephalus*", *Biochimica et Biophysica Acta*, vol. 997, pp. 55–64, 1989.

Schrag, J. D., et al., "Primary secondary structure of antifreeze peptides from arctic and antarctic zoarcid fishes", *Biochimica et Biophysica Acta*, vol. 915, pp. 357–370, 1987.

DeVries, A., et al., "Structure of a Peptide Antifreeze and Mechanism of Adsorption to Ice", *Biochimica et Biophysica Acta*, vol. 495, pp. 388–392, 1977.

DeVries, A. L., et al., "Role of glycopeptides and peptides in inhibition of crystallization of water in polar fishes", *Phil. Trans. R. Soc. Lond.*, vol. B304, pp. 575–588, 1984.

DeVries, A. L., et al., "Role of glycopeptides in inhibition of crystallization of water in polar fishes", *Phil. Trans R. Soc. Lond.*, vol. B304, pp. 575–588, 1984.

Knight, C. A., et al., "Melting Inhibition and Superheating of Ice by an Antifreeze Glycopeptide", *Science*, vol. 245, pp. 505–507, 1989.

Feeney, R. E., "Inhibition and Promotion of Freezing: Fish Antifreeze Proteins and Ice–Nucleating Proteins", *Comments Agric. & Food Chemistry*, vol. 1, No. 3, pp. 147–181, 1988.

Brown, R. A., et al., "Direct Evidence for Antifreeze Glycoprotein Adsorption Onto an Ice Surface", *Biopolymers*, vol. 24, pp. 1265–1270, 1985.

Li, Xiao–Mao, et al., "Structure of an Antifreeze Polypeptide and its Precursor from the Ocean Pout, *Macrozoarces americanus*", *The Journal of Biological Chemistry*, vol. 260, No. 24, pp. 12904–12909, 1985.

Gourlie, B., et al., "Winter Flounder Antifreeze Proteins: A Multigene Family", *The Journal of Biological Chemistry*, vol. 259, No. 23, pp. 14960–14965, 1984.

Davies, P. L., "Antifreeze Protein Genes of the Winter Flounder", *The Journal of Biological Chemistry*, vol. 259, No. 14, 1984.

(List continued on next page.)

OTHER PUBLICATIONS of winter flounder antifreeze cDNA", *Proc. Natl. Acad. Sci.*, vol. 78, pp. 2825–2529, Mar. 1981.

Raymond, J. A., et al., "Inhibition of Growth of Non-basal Planes in Ice by Fish Antifreezes", *Proc. Natl. Acad. Sci.*, vol. 86, pp. 881–885, Feb. 1989.

Davies, P. L., et al., "DNA Sequence Coding for an Antifreeze Protein Precursor from Winter Flounder", *Proc. Natl. Acad. Sci.*, vol. 79, pp. 335–339, Jan. 1982.

Hew, C. L., et al., "Presence of Cystine-Containing Antifreeze Proteins in the Spruce Budworm", *Can. J. Zool.*, vol. 61, pp. 2324–2328, 1983.

Steponkus, P. L., "Role of the Plasma Membrane in Freezing Injury and Cold Acclimation", *Ann. Rev. Plant Physiol.*, 1984, 35: 543–584.

DeVries, A. L., "Antifreeze Peptides and Glycopeptides in Cold Water Fishes", *Ann. Rev. Physiol.*, 1983, 45: 245–260.

Duman, J., et al., "The Role of Hemolymph Proteins in the Cold Tolerance of Insects", *Ann. Rev. Physiol.*, 1983, 45: 261–270.

Burke, M. J., et al., "Freezing and Injury in Plants", *Ann. Rev. Plant Physiol.*, 1976, 27: 507–528.

Pain, R. H., "Helices of Antifreeze", *Nature*, vol. 333, 19 May 1988, pp. 207–208.

Peterson, I., "Fish Antifreeze with an Electrical Twist", *Science News*, vol. 133, p. 325.

MacFarlane, D. R., et al., "Recent Insights on the Role of Cryoprotective Agents in Vitrification", *Cryobiology*, 27, 345–358 (Feb. 1990).

Harrison, K., "Ice Growth in supercooled solutions of antifreeze glycoprotein", *Nature*, vol. 328, No. 6127, pp. 241–243, 1987.

Ananthanarayanan, V. S., "Antifreeze Proteins: Structural Diversity and Mechanism of Action", *Life Chemistry Reports*, vol. 7, pp. 1–32, 1989.

Franks, F., et al., "Antifreeze activity of Antarctic fish glycoprotein and a synthetic polymer", *Nature*, vol. 325, No. 8, pp. 146–147, 1987.

Yang, D. S. C., et al., "Crystal structure of an antifreeze polypeptide and its mechanistic implications", *Nature*, vol. 333, No. 19, pp. 232–237, 1988.

Mimata, T., et al., "Effect of noradrenaline on current- and voltage-clamped muscle cells of the guinea-pig vas deferens in normal Krebs solution", *European Journal of Pharmacology*, vol. 163, pp. 181–185, 1989.

Kimblad, et al., "High Potassium Contents in Organ Preservation Solutions Cause Strong Pulmonary Vasocontraction", *Ann Thorac Surg*, vol. 52, pp. 523–528, 1991.

Kao, M. H., "The Relationship between molecular weight and antifreeze polypeptide activity", *Can. J. Zoo*, vol. 64, pp. 578–582, 1986.

Fletcher, G. L., "Antifreeze peptides confer freezing resistance to fish", *Can. J. Zoo*, vol. 64, pp. 1897–1901, 1986.

DeVries, A. L., et al., "Freezing Resistance in Some Antarctic Fishes", *Science*, vol. 163, pp. 1073–1075, 1969.

Powers, D., "Fish as Model Systems", *Science*, vol. 246, pp. 352–358, 1989.

Pickett, G. S., et al., "Sequence of an antifreeze protein precursor", *J. Biochem*, vol. 143, pp. 35–38, 1984.

Knight, C. A., et al., "Fish Antifreeze protein and the freezing and recrystallization of ice", *Nature*, vol. 308, No. 5956, pp. 295–296, 1984.

Lin, Y., et al., "Molecular cloning and characterization (List continued on next page.)

OTHER PUBLICATIONS

De Antoni, G. L., "Trehalose, A Cryoprotectant for *Lactobacillus bulgaricus*", *Cryobiology*, 26, 149–153 (1989).

Morris, G. J., et al., "Freezing Injury in *Saccharomyces cerevisiae*", *Cryobiology* 25, 471–482, 1988.

Knight, C. A., et al., "Solute Effects on Ice Recrystallization: An Assessment Technique", *Cryobiology* 25, 55–60, 1988.

Knight, C. A., et al., "Inhibition of Recrystallization of Ice by Insect Thermal Hysteresis Proteins: A Possible Cryoprotective Role", *Cryobiology* 23, 256–262, 1986.

Chaw, M. W., et al., "Cryomicroscopic Observations on Directional Solidification in Onion Cells", *Cryobiology*, 22, 392–399, 1985.

Rubinsky, B., et al., "A Cryomicroscope Using Directional Solidification for the Controlled Freezing of Biological Material", *Cryobiology* 22, 55–68, 1985.

Collins, G. M., et al., "Studies in Cryoprotection: A Simple Method for the Controlled Introduction and Removal of Cryoprotective Agents During Organ Perfusion", *Cryobiology*, 21, 1–5, 1984.

Lin, Y., et al., "Compartmentalization of NaCl in Frozen Solutions of Antifreeze Glycoproteins", *Cryobiology* 13, pp. 334–340, 1976.

Sundberg, R., et al., "The Functional Effects of Suppression of Hypothermia–Induced Cell Swelling in Liver Preservation by Cold Storage", *Cryobiology* 28, 150–158, 1991.

Rubinsky, B., et al., "The Effect of Antifreeze Glycopeptides on Membrane Potential Changes at Hypothermic Temperatures", *Biochem. and Biophys. Res. Comm.*, vol. 173, No. 3, pp. 1369–1374, Dec. 31, 1990.

Hew, C. L., "Structures of Shorthorn Sculpin Antifreeze Polypeptides", *Biochem*, 151, 167–172, 1985.

Raymond; J. A. et al., "Absorption Inhibition as a Mechanism of Freezing Resistance in Polar Fishes", *Proc. Natl. Acad. Sci.*, vol. 74, No. 6, pp. 2589–2593, Jun. 1977.

INTERACTION OF THERMAL HYSTERESIS PROTEINS WITH CELLS AND CELL MEMBRANES AND ASSOCIATED APPLICATIONS

GOVERNMENT RIGHTS

This invention was made at least in part with United States Government support under Grant Nos. CTS8918863 and CTS8914832, awarded by the National Science Foundation. The United States Government has certain rights in this invention.

CROSS REFERENCE TO RELATED APPLICATIONS

This application is a continuation-in-part of co-pending applications Ser. No. 07/910,151, filed Jul. 16, 1992, now abandoned, Ser. No. 07/910,254, filed Jul. 16, 1992, now abandoned and Ser. No. 07/562,461, filed Aug. 3, 1990, now abandoned. Application Ser. No. 07/562,461, filed Aug. 3, 1990, is a continuation-in-part of application Ser. No. 07/466,050, filed Jan. 17, 1990, now abandoned.

RELATED INTERNATIONAL APPLICATIONS

Application Ser. No. 07/910,254, filed Jul. 16, 1992, is based on international application no. PCT/US91/00351, filed Jul. 17, 1991, which claims priority of applications Ser. No. 07/466,050 and Ser. No. 07/562,461. Application Ser. No. 07/910,151, filed Jul. 16, 1992, is based on international application no. PCT/US91/00452, filed Jan. 17, 1992, which claims priority of applications Ser. No. 07/466,050 and Ser. No. 07/562,461 and international application no. PCT/US91/00351.

This application lies in the field of the treatment of mammalian cells and the protection of their viability upon exposure to a variety of conditions which would otherwise do damage to the cells. This invention also lies in the field of peptides and glycopeptides known as thermal hysteresis proteins or antifreeze proteins.

BACKGROUND OF THE INVENTION

The existence of naturally-occurring macromolecular species known as "antifreeze proteins" or "thermal hysteresis proteins" and the subclassifications "antifreeze glycoproteins" and "antifreeze polypeptides" is well known and widely reported in the literature. The discovery of antifreeze glycoproteins, for example, was first reported by DeVries, A. L., et al., in "Freezing Resistance in Some Antarctic Fishes," *Science* 163:1073–1075 (Mar. 7, 1969). DeVries, et al. observed that water temperatures in McMurdo Sound, Antarctica, average −1.87° C. over the year, and that various species of fish survive in these conditions despite the fact that the total concentration of sodium chloride and other low molecular weight substances present in the blood sera of these fish could only produce a freezing point depression of less than half that needed for survival under these conditions. While earlier studies had indicated that the survival of these fish might be attributable to the presence of certain macromolecular antifreeze compounds in the blood of the fish, DeVries and his coworkers were the first to establish the nature and composition of these macromolecular species. With typical molecular weights ranging from about 2,500 to about 34,000, these species are now referred to as antifreeze glycopeptides or "AFGPs." Further investigations have revealed that many species of north temperate and Arctic fishes carry antifreeze compounds in their blood. Some of these compounds are glycoproteins while others contain no sugar moieties and are referred to as antifreeze polypeptides or "AFPs," having molecular weights ranging from about 3,300 to about 12,000.

Some of the common features of AFGPs and AFPs are as follows:

(a) They are present in relatively large concentrations in fish blood (about 10–40 mg/mL). In fish that experience seasonal changes in temperature, the compounds are present in low concentrations, or are absent entirely, throughout much of the year, increasing to higher levels during seasonal periods of low water temperature and low photoperiod. In fish residing in Antarctic regions where the waters remain at subfreezing temperatures, the compounds remain present throughout the year, in high concentrations.

(b) The compounds achieve freezing-point depression in a non-colligative manner (i.e., the effect varying with molecular size but not the number of molecules present) and to a far greater degree than one would expect on the basis of the osmolality of the solution containing the molecules.

(c) While the compounds lower the freezing point, the melting point remains unaffected (i.e., they exhibit thermal hysteresis behavior).

(d) The compounds function by interacting with and modifying the morphology of ice crystals.

Because of the thermal hysteresis effect, the compounds are generically referred to herein for convenience as "thermal hysteresis proteins."

Prior to the present invention, studies relating to thermal hysteresis proteins have focused on (a) the isolation and characterization of the proteins,
(b) the conformations of the protein molecules, including second and higher order conformations,
(c) the interaction of the protein molecules with ice, and
(d) means of preparing the proteins synthetically including methods involving the use of recombinant DNA.

The only investigations into biological functions and utilities of the proteins are the studies of the interaction of the protein molecules with ice. These studies have addressed such matters as the thermodynamics and surface kinetics of the ice crystal surfaces, the direction of crystal growth, and the modes and directions by which the proteins block the crystal growth.

Shortly after the discovery of the proteins, attempts were made to exploit the proteins' antifreeze character by using them in biological materials other than those of the fish from which they were derived. As an example, red blood cells were treated with the proteins using standard cryopreservation procedures and exposed to freezing conditions. The results were not favorable, however, since the proteins caused the complete destruction of the cells rather than their preservation. There has been no evidence that the proteins could be successfully used with biological materials other than the fish to which they were native.

In summary, prior to the present invention no studies have been performed on properties or utilities of the proteins in contexts unrelated to ice crystals. Nor have there been studies which have demonstrated or suggested any potential benefit that these proteins might offer to organisms other than fish, and particularly to mammalian organisms and tissues. Furthermore, no studies have been conducted which suggest that these proteins might have any beneficial effect at all at concentrations significantly below the concentrations in which they are found in the fish. In fact, the well-recognized and extensively reported non-colligative character of these proteins discourages any suggestion that either injurious or beneficial effects attributable to these proteins might vary with concentration.

SUMMARY OF THE INVENTION

The present invention resides in the discovery of a heretofore unrecognized and unutilized quality of thermal hysteresis proteins—their ability to interact with cells and cell membranes. The interaction occurs with cell membranes in a wide range of structures, including individual cells in cell suspensions, connected cell masses in tissues and organs, and cell structures which are pervaded with a vascular system. The interaction is a favorable one, imparting to the cell membranes and the structures which incorporate these membranes a variety of benefits, including improvements in cell viability and survival rate, prolongation of the functionality, stability and structural integrity of the cells and cell tissues, reduction of the occurrence of structural damage to membranes and cells under adverse conditions, and control of the transport of ions across the cell membranes.

The various types of interaction which are the subject of this invention are unrelated to the known effects of these proteins on ice crystal propagation, since the beneficial effects of these interactions are observed under conditions where ice crystals do not form at all, in addition to their occurrence in the presence of ice crystals. For example, benefits are observed at temperatures ranging from cryogenic temperatures to temperatures well above physiological temperatures. The invention thus extends to situations involving physiological conditions as well as nonphysiological conditions, and to situations that involve the presence of ice crystals as well as those in which ice crystals are completely absent. Nonphysiological conditions in which beneficial effects on viable cells and cell membranes are observed therefore include:

(i) hypothermal conditions defined by temperatures above the normal freezing point of water (0° C.), and therefore with no possibility of ice formation, and below the physiological temperature of the cells;

(ii) vitrification conditions defined by temperatures at or below the glass formation (or glass transition) temperature, such as for example from 150K down to about 4K, and by the presence of vitrifying agents which promote vitrification and inhibit crystallization;

(iii) freezing conditions, such as temperatures from the normal freezing point of water down to about 4K, which permit the formation of ice crystals;

(iv) hyperthermal conditions defined by temperatures above the physiological temperature of the cells, for example temperatures within the range of the physiological temperature up to about 10° C. above the physiological temperature; and (v) conditions defined by chemical environments which differ from the physiological chemical environment of the cells, such as conditions of nonphysiological pH and other variations from the physiological chemical composition, as well as such conditions in combination with conditions of nonphysiological temperature.

Applicability of the invention aim extends to abnormal physiological conditions such as diseases associated with the instability of cell membranes and diseases associated with imbalances of ions between intracellular and extracellular spaces giving rise to abnormal ion transport across the cell membranes. The unexpected nature of this behavior is heightened by the discovery that the blockage of ion channels, such as for example those of calcium and potassium ion in epithelial cells, is achieved without interference with other metabolic functions of the cells, including ATP ion pumps and interactions with carbachol. Still further, the invention offers benefits to cells in normal physiological conditions, such as through the use of cosmetics or medications designed to restore, preserve or repair epidermal tissue. Further still, the invention finds application in the preservation of foods which would otherwise lose their appeal due to the breakdown of cell structures and functions in the foodstuffs.

The invention finds applicability to a wide range of living cells, including both animal cells and plant cells. A particularly unusual and interesting discovery in connection with the present invention, however, is the utility of the thermal hysteresis proteins in the treatment and preservation of mammalian cells, tissues and organs. In their natural form, these proteins exist in non-mammalian species only, and the differences in cell and membrane structure as well as in blood and cytoplasm composition between these species and mammalian species renders the presently discovered benefits surprising and unexpected. The invention is thus of particular interest and utility as applied to mammalian cells, tissues, organs and organisms which are exposed to conditions which differ from the normal physiological condition of the mammal. Examples of cells to which the invention is applicable are mammalian oocytes, hepatocytes, erythrocytes and leukocytes, and various types of plant cells. Examples of tissues and organs are tissue of livers, hearts, and kidneys, and the organs themselves. Examples of organisms are embryos, self-sustaining whole animals, plant seeds and whole plants.

One of the key discoveries in this invention is the means by which the proteins caused the destruction of biological cells in the early studies on non-fish cells. This invention establishes that the destruction arises from the mechanical shearing effect of the spicular ice crystals which are formed as a result of the effect of the proteins in restricting the crystal growth to the c-axis.

This discovery is unexpected since the destruction does not occur in the native fish species but only in cellular suspensions. A consequence of this discovery is the ability of the proteins to achieve a protective rather than destructive effect at sub-freezing temperatures when used at concentrations lower than the natural concentrations, or when used under conditions in which vitrification occurs, or both. Accordingly, the proteins offer benefits at concentrations which are considerably lower than those at which they are present in their natural source organisms, a feature which could not be predicted from the mere knowledge of their existence in those organisms. Furthermore, in biological systems other than the native systems of the proteins, the proteins offer benefits at these low concentrations which are not seen at the higher, natural concentrations.

A further consequence of the discovery of the mode of mechanical damage is that the protective effect can be achieved in the freezing of whole organs by introducing the proteins into an organ through the organ's vascular system. The spicular ice crystals propagate freely in the vascular system, limited only by the walls of the blood vessels, while the proteins penetrate into the interstitial areas to contact the cell membranes, where they provide protection from the damage which would otherwise occur from the low temperature.

Additional benefits arising from the invention are many and varied. Included among these are the elimination of the need to maintain a fast cooling rate during freezing to cryogenic temperatures, the ability of the proteins to raise the viscosity of solutions at considerably lower concentrations than known cryoprotectants, and the ability of the proteins to preserve foods upon freezing. Other advantages, benefits, and applications of the present invention will be apparent from the description which follows.

DETAILED DESCRIPTION OF THE INVENTION AND PREFERRED EMBODIMENTS

1. DEFINITIONS

The following terms are used in this specification with the following definitions:

"Abnormal" or "nonphysiological conditions" for cells, tissues, organs or organisms refer to conditions which differ from the normal physiological conditions. Abnormal or nonphysiological conditions include, but are not limited to, a temperature which is significantly higher or lower than the normal physiological temperature of the healthy organism of which the cell, tissue or organ is native, or the organism itself; an excess or subnormal amount of carbon dioxide, oxygen, inorganic salts, or organic compounds, a pH value significantly higher or lower than that of the healthy organism, and combinations of these conditions.

"Antifreeze proteins," "antifreeze polypeptides" ("AFPs"), "antifreeze glycoproteins" and "antifreeze glycopeptides" ("AFGPs") refer to macromolecules found in the body fluids of some animals, which have the commonly known property that they reduce non-colligatively the freezing point of water.

Antifreeze proteins, polypeptides, glycoproteins and glycopeptides are also known as "thermal hysteresis proteins" because the temperature at which freezing occurs is depressed to a greater degree than one could attribute to any colligative character of the proteins, whereas the temperature at which ice melts during melting is depressed is significantly less, in accordance solely with colligative behavior.

"Cryogenic temperatures" refers to temperatures below 0° C.

"Freezing" refers to the transition from the liquid phase of water to the solid phase of water.

"Hyperthermic" refers to temperatures higher than the normal physiological temperature of a cell, tissue, organ or organism, such as for example from slightly above the physiological temperature up to about 20° C. above, preferably to about 10° C. above, and more preferably to about 5° C. above the physiological temperature.

"Hypothermic" refers to temperatures lower than the normal physiological temperature of a cell, tissue, organ or organism, but not low enough to cause a phase transition to the solid phase.

"Isolated and purified" refers to molecular species which are extracted from the organism in which they naturally occur, and concentrated by conventional laboratory techniques such as chromatography, preferably to a concentration of at least about 85%, more preferably to at least about 95%. This invention further extends to molecules which have a molecular structure which is either the same, highly similar, or homologous to naturally occurring forms of the molecules, and which may have been synthesized either by chemical means or by recombinant DNA techniques.

"Mammal" refers to any warm blooded mammal as the term is generally used in biology, including, for example, pig, cow, rabbit, horse and human being.

"Polar fish species" refers to cold-blooded aquatic animals, particularly vertebrates, which reside in waters of the polar regions of the earth, including the regions within the Arctic and Antarctic Circles. Polar fish species of particular interest in connection with this invention are those which remain in waters which become or remain ice-laden.

"Spicule" and "spicular" refer to ice crystals and ice crystal growth in which the dominant direction of crystal propagation is along the c-axis, i.e., perpendicular to the basal plane, to form crystals having a needle-like shape.

"Viable" means capable of living, capable of surviving and developing under, or upon a return to, normal physiological conditions, or capable of germinating under conditions normally favorable to germination.

"Vitrification" refers to solidification at cryogenic temperatures in such a manner that a glass phase, i.e., a non-crystalline solid, is formed, as opposed to crystalline ice. "Apparent vitrification" refers to vitrification as determined by visual observation under a microscope. Vitrification of a biological material is generally achieved by introducing any of a variety of cryoprotective or "vitrifying" agents, including polyhydric alcohols such as glycerol and propylene glycol, or other compounds such as dimethylsulfoxide into the material. The introduction of vitrifying agents is often accompanied by relatively high rates of cooling. The optimal rates in each case vary with the composition and thermodynamics of the system. Typical cooling rates in most cases for small unorganized cells such as ova, sperm, and embryos, and for organs, generally fall within the ranges of about 100° C./min to about 2,000° C./min, preferably about 200° C./min to about 1,750° C./min, and more preferably about 700° C./min to about 1,750° C./min. Rates on the order of 1500° C./min are commonly used.

2. THERMAL HYSTERESIS PROTEINS—SOURCE, TYPE AND STRUCTURE

Thermal hysteresis proteins have been isolated from a wide variety of sources, and these sources and the structures of the various proteins obtained from them have been reported extensively in the literature. The sources include both fish species and non-fish species, and are listed in Tables I and II below.

TABLE I

| THERMAL HYSTERESIS PROTEINS OF FISH SPECIES | | |
|---|---|---|
| Protein Type, Composition and Size | Source Fish Species | Trivial Name of Fish species |
| Antifreeze glycoproteins (AFGPs): contain alanine, threonine | Antarctic notothenioids: *Pagothenia borchgrevinki* | |

TABLE I-continued

THERMAL HYSTERESIS PROTEINS OF FISH SPECIES

| Protein Type, Composition and Size | Source Fish Species | Trivial Name of Fish species |
|---|---|---|
| and GalGalNAc disaccharide. M.W.: 2,600-33,700 | *Trematomus borchgrevinki* *Dissostichus mawsoni* Northern ocean gadoids: | Antarctic cod |
| | *Gadus agac* | Greenland cod |
| | *Gadus morhua* | Atlantic cod |
| | *Microgadus tomcod* | Atlantic tomcod |
| | *Boreogadus saida* | Arctic polar cod |
| | *Eligenus gracilis* | Saffron cod |
| Antifreeze Polypeptides (AFPs), Type I: alanine-rich; M.W.: 3,300-6,000 | Righteye flouders: *Pseudopleuronectus americanus* *Limanda ferruginea* Cottids: | Winter flounder Yellowtail flounder |
| | *Myoxycephalus scorpius* | Shorthorn sculpin |
| | *Myoxycephalus aenaeus* | Grubby sculpin |
| | *Myoxycephalus scorpiodes* | Arctin sculpin |
| Antifreeze Polypeptides (AFPs), Type II: cysteine-rich; homologous to C-type lectins; M.W.: 14,000-16,000 | Cottid: *Hemitripterus americanus* *Osmerus mordex* *Clupea harengus harengus* | Sea raven Smelt Herring |
| Antifreeze Polypeptides (AFPs), Type III: no cysteines, and not rich in alanines; M.W.: 5,000-6,700 | Eel pouts: *Macrozoarces americanus* *Rhigophila dearborni* *Lycodes polaris* | Ocean pout Antarctic eel pout Arctic eel pout |

TABLE II

NON-FISH SOURCES OF THERMAL HYSTERESIS PROTEINS

| A. Insects Other Than Beetles: | |
|---|---|
| Order | Species |
| Collembola | 7 spp. |
| Plecoptera | *Arcynopteryx compacta* |
| Orthoptera | *Parcoblata pennsylvanica* |
| Hemiptera | *Oncopeltus fasciatus* |
| Mecoptera | *Boreus westwoodi* |
| Lepidoptera | *Choristoneura fumiferana* |

| B. Cleoptera (Beetles): | |
|---|---|
| Family | Species |
| Tenebrionidae | *Tenebrio molitor* *Mercantha contracta* *Uloma impressa* *Playdema sp.* |
| Elateridae | *Ampedus lineatus* *Ampedus sp.* *Lepidotus discoideus* *Melanotus sp.* |
| Cucjidae | *Cucujus clavipes* |
| Pyrochridae | *Dendroides canadensis* |
| Lampyridae | *Photinus sp.* |
| Coccinellidae | *Coccinella novemnotata* |
| Scolytidae | *Ips acuminatus* |
| Cerambycidae | *Rhagium inquisitor* |

| C. Non-Insect Arthropods: | |
|---|---|
| Animal | Species |
| Spiders | *Philodromus sp.* *Clubiona sp.* *Bolyphantes index* |
| Centipede | *Lithobius forficatus* |
| Mite | *Alaskozetes antarcticus* |

| D. Other Invertebrates: | |
|---|---|

TABLE II-continued

NON-FISH SOURCES OF THERMAL HYSTERESIS PROTEINS

| Mussel | *Mytilus edulis* |
|---|---|

The thermal hysteresis proteins which have been the most extensively studied, and which are the preferred proteins for use in the practice of the present invention, are those isolated from fish species. As indicated in Table I, these proteins include both glycosylated proteins (AFGPs) and non-glycosylated proteins (AFPs), and the latter fall within three general categories, designated Type I, Type II, and Type III.

The AFGPs generally consist of a series of repeats of the tripeptide unit alanyl-threonyl-alanyl, with the disaccharide $\beta$-D-galactosyl-(1→3)-$\alpha$-N-acetyl-D-galactosamine attached to the hydroxyl group of the threonine residue, although variations exist. For example, AFGPs of relatively low molecular weight contain proline and arginine residues in place of some of the alanine and threonine residues, respectively. Chromatographic studies of the AFGPs from representative fish species have revealed eight major molecular weight fractions, as indicated in Table III.

TABLE III

Molecular Weight Fractions of AFGPs From *Pagothenia borchgrevinki*

| Fraction No. | Molecular Weight |
|---|---|
| 1 | 33,700 |
| 2 | 28,800 |
| 3 | 21,500 |
| 4 | 17,000 |
| 5 | 10,500 |
| 6 | 7,900 |
| 7 | 3,500 |
| 8 | 2,600 |

The AFPs differ from one another to a larger degree than do the AFGPs. As indicated in Table I, the three types of AFPs differ from each other in their residue content. Type I AFPs are rich in alanine residues (about 65%), with most of the remainder consisting of polar residues such as aspartic acid, glutamic acid, lysine, serine and threonine. The molecular weight ranges from about 3,300 to about 6,000. Type II AFPs are considered to be rich in cysteine (actually half-cysteine) residues, and are homologous to C-type lectins. Type II AFPs from the sea raven contain 7.6% cysteine, 14.4% alanine, 19% total of aspartic and glutamic acids, and 8% threonine. The molecular weight ranges from about 14,000 to about 16,000. Type III AFPs are devoid of cysteine residues and not rich in alanine residues. No conspicuous dominance of any particular amino acid is evident, and the amino acid content is evenly divided between polar and non-polar residues. The molecular weight ranges from about 5,000 to about 6,700. All percents referred to in this paragraph are on a mole basis.

Thermal hysteresis proteins from insects are primarily AFPs of Type II, and typical compositions in terms of amino acid residues are those of the *Choristoneura fumiferana* (spruce budworm) and *Tenebrio molitor* (beetle). These are listed in Table IV, which also includes the amino acid composition of the sea raven for comparison.

TABLE IV

Comparative Amino Acid Compositions of Type II AFPs

| Amino Acid Residue | Spruce Budworm Fraction II | Beetle | Sea Raven |
|---|---|---|---|
| Asx | 9.5 | 5.3 | 10.7 |
| Thr | 6.0 | 2.3 | 7.9 |
| Ser | 13.0 | 11.1 | 8.2 |
| Pro | 5.0 | 0.0 | 6.7 |
| Glx | 11.0 | 12.4 | 9.1 |
| Gly | 15.0 | 11.4 | 8.1 |
| Ala | 8.0 | 5.0 | 14.4 |
| ½-Cys | 6.0 | 28.0 | 7.6 |
| Val | 3.0 | 2.3 | 1.2 |
| Met | 0.0 | 0.0 | 5.4 |
| Ile | 1.2 | 1.0 | 1.7 |
| Leu | 6.5 | 2.2 | 6.2 |
| Tyr | 1.0 | 0.0 | 1.2 |
| Phe | 2.2 | 0.0 | 2.0 |
| Lys | 3.1 | 15.4 | 2.1 |
| His | 0.0 | 3.1 | 2.5 |
| Trp | 0.0 | 0.0 | 2.8 |
| Arg | 8.0 | 0.0 | 2.3 |

Thermal hysteresis proteins may be extracted from the sera or other bodily fluids of the organisms to which they are native by conventional means. Isolation and purification of the proteins may be achieved by chromatographic means, as well as by absorption, by precipitation, and by evaporation. Other means, many of which are described in the literature, will be readily apparent to those skilled in the art.

Thermal hysteresis proteins may also be produced synthetically, either by conventional chemical synthesis methods or by methods involving recombinant DNA. The DNA coding sequences of the genes which form these proteins have been elucidated and are extensively reported. See, for example, DeVries, A. L., et al., *J. Biol. Chem.* 246:305 (1971); Lin, Y., et al., *Biochem. Biophys. Res. Commun.* 46:87 (1972); Yang, D. S. C., et al., *Nature* 333:232 (1988); Lin, Y., *Proc. Natl. Acad. Sci. U.S.A.* 78:2825 (1981); Davies, P. L., et al., *J. Biol. Chem.* 79:335 (1982); Gourlie, B., et al., *J. Biol. Chem.* 259:14960 (1984); Scott, G. K., et al., *Can. J. Fish. Aquat. Sci.* 43:1028 (1986); Scott, G. K., et al., *J. Mol. Evol.* 27:29 (1988). Successful microinjection of the AFP gene into species other than its native species has been reported. See, for example, Zhu, Z, et al., *Angew. Ichthyol.* 1:31 (1985); *Kexue Tongbao* 31:988 (1986); Chourrout, D., et al., *Aquaculture* 51:143 (1986); Dumman, R. A., et al., *Trans. Am. Fish. Soc.* 116:87 (1987); Fletcher, G. L., et al., *Can. J. Fish Aquat. Sci.* 43:352 (1988); Maclean, N. D., et al., *Bio Technology* 5:257 (1987); Stuart, G. W., et al., *Development* 103:403 (1988); McEvoy, T., et al., *Aquaculture* 68:27 (1988); Ozato, K, et al., *Cell Differ.* 19:237 (1986).

3. METHODS OF FORMULATION AND USE

In the practice of the present invention, the thermal hysteresis proteins are generally used in the form of a liquid solution, and preferably an aqueous solution. The thermal hysteresis proteins may be used individually or in combination. When the proteins are used in combination, it will often be most convenient to use the proteins in the physiological combinations in which they naturally occur in the source species, i.e., the same mixture and proportions of the protein species as they are found in the fluid of the fish, insect or other organism from which they are extracted, although isolated from other components of the fluid and redissolved in a different solvent or solution, perhaps at a total concentration which differs from that in which the mixture is present in its natural environment. In certain cases, however, activity and effectiveness may be improved by fractionating the proteins in the source mixture and selecting and recombining fractions in an optimal manner.

The concentration of the thermal hysteresis proteins in the liquid solution as used in the present invention may vary widely, although in certain cases, improved results will be obtained within certain concentration ranges, and in certain cases, the concentration must be restricted to certain ranges to avoid injury caused by the proteins themselves. In general, however, the proteins will be used in concentrations of from about 0.01 mg/mL to about 80 mg/mL, preferably from about 0.1 mg/mL to about 60 mg/mL, more preferably from about 1 mg/mL to about 40 mg/mL, and most preferably from about 1 mg/mL to about 20 mg/mL. When used with human cells, particularly under temperatures below the physiological temperature of the cells, preferred concentrations are from about 0.1 mg/mL to about 40 mg/mL, more preferably from about 0.1 mg/mL to about 3 mg/mL. In applications where the proteins are used to protect tissue at temperatures below the physiological temperature of the tissue, preferred concentrations are within the range of about 0.1 mg/mL to about 50 mg/mL, and when the tissue is human tissue, preferred concentrations are within the range of about 0.1 mg/mL to about 3 mg/mL. In applications where the proteins are used to protect cells in general at temperatures below the physiological temperature of the cells but above the freezing temperature of the cells, or below the freezing temperature of the cells but in the presence of a vitrifying agent or other non-peptide cryoprotectant, preferred concentrations are within the range of about 0.01 mg/mL to about 60 mg/mL, and more preferred concentrations are within the range of about 1 mg/mL to about 40 mg/mL. In applications where the proteins are used to block ion channels across cell membranes, preferred concentrations are at least about 0.01 mg/mL, more preferably at least about 0.1 mg/mL, and most preferably from about 0.5 mg/mL to about 40 mg/mL. All concentrations of thermal hysteresis proteins in this specification are expressed as totals of the concentrations of individual thermal hysteresis proteins when a solution contains a mixture of different thermal hysteresis proteins.

Aqueous solutions of the thermal hysteresis proteins for use in the present invention may further contain any of the wide variety of mixtures of salts, sugars, ions and other nutrients which are included in electrolyte solutions known in the art to be useful for preserving biological agents. These include tissue culture media, organ perfusion fluids, and the like. Electrolyte solutions are particularly useful for enhancing the biological compatibility of the proteins. Examples of the many electrolyte solutions known in the art are:

Physiological Saline, in which the NaCl concentration is either 0.9% or 0.95%

Ringer's Injection Solution (U.S.), listed in *Facts and Comparisons*, p. 50, Lippincott Publishing Co., St. Louis, Mo. (October 1981)

Mammalian Ringer's Solution (U.K. and Canada), listed by Best and Taylor, Basis of Medical Practice, 6th ed., Baltimore (1950)

Lactated Ringer's Solution (U.S.), listed in *Facts and Comparisons*, p. 50, Lippincott Publishing Co., St. Louis, Mo. (October 1981)

Lactated Ringer's Solution (Hartmann), listed by Hartmann, A. F., *J. Am. Med. Assoc.* 103:1349–1354 (1934)

Acetated Ringer's Solution, listed by Fox, C. L., et al., *J. Am. Med. Assoc.* 148:825–833 (1952)

Locke's Solution, listed by Locke, F. S., *Zbl. Physiol.* 8:166 (1894); 14:670 (1900); 15:490 (1901)

Tyrode's Solution, listed by Tyrode, M. J., *Arch. Int. Pharmacodyn.* 20:205 (1910)

Krebs Henseleit Solution, listed by Krebs, H. A., et al., *Hoppe-Seyle's Z. Physiol. Chem.* 210:33–66 (1932)

Krebs Ringer Phosphate Solution, listed by Krebs, H. A., *Hoppe-Seyle's Z. Physiol. Chem.* 217:193 (1933)

Krebs Serum Substitute Solution, listed by Krebs, H. A., *Biochem. Biophys. Acta* 4:249–269 (1950)

Krebs Improved Ringer II Solution, listed by Krebs, H. A., *Biochem. Biophys. Acta* 4:249–269 (1950)

Krebs Improved Ringer III Solution, listed by Krebs, H. A., *Biochem. Biophys. Acta* 4:249–269 (1950)

Krebs Liver Perfusion Solution with Bovine Serum Albumin and Red Cells, listed by Hem, R., et al., *Biochem. J.* 101:284 (1966)

Schimassek Liver Perfusion Solution, listed by Schimassek, H., et al., *Biochem. Z.* 336,440 (1963)

Krebs Kidney Perfusion Solution, listed by Nishiitsutsuji-Uwo, J., et al., *Biochem. J.* 103:852–862 (1967)

Hepatocyte Incubation Solution, listed by Crow, K. E., et al., *Biochem. J.* 172:29–36 (1978)

Bahlman Kidney Perfusion Solution, listed by Bahlman, J., et al., *Am. J. Physiol.* 212:77 (1967)

Fulgraff Kidney Perfusion Solution, listed by Fulgraff, et al., *Arch. Int. Pharmacodyn.* 172:49 (1972)

The optimal choice of electrolyte solution for any particular application will vary with the application, such as, for example, the form of the cells (whether the cells are present as cell suspensions, tissues, or organs) to be treated or protected by the thermal hysteresis proteins, the animal from which the cells are derived, and the conditions to which the cells have been, or are expected to be, exposed.

In embodiments of the invention involving vitrification conditions, the thermal hysteresis proteins are used in combination with vitrifying agents which prevent or inhibit ice crystal formation during solidification of the intracellular and extracellular fluids upon cooling to sub-freezing temperatures. Various vitrifying agents are known in the art, and may be used either individually or in combination with other vitrifying agents or biologically compatible solutes. Examples of vitrifying agents are glycerol, dimethyl sulfoxide, ethylene glycol, polyvinylpyrrolidone, glucose, sucrose, propanediol, butanediol, and carboxymethyl cellulose. Polyhydric alcohols as a class are useful as vitrifying agents. Prominent examples are glycerol, ethylene glycol, propanediol, butanediol, and butanetriol. Concentrations of vitrifying agents may vary widely, depending on the concentrations of other components in the system, the cooling rate and the lowest temperature reached. In general, best results will be obtained with concentrations of from about 5% to about 35% by weight. Vitrification is usually practiced with a rapid cooling rate, such as for example a rate exceeding 100° C./min, and preferably exceeding 1,000° C./min.

In embodiments which involve the use of non-peptide cryoprotectants, without necessarily avoiding the formation of ice crystals, many of the same considerations apply. The agents listed above as examples of vitrifying agents serve as well as cryoprotectants, within similar concentration ranges.

The beneficial effect of the thermal hysteresis proteins on cells and/or cell membranes is achieved by placing the proteins in contact with the cells and maintaining such contact throughout, or for a substantial portion of, the period of exposure to otherwise injurious conditions. When the cells are in the form of cell suspensions, contact of this type is achieved by simply adding the proteins to the suspension fluid. When the cells are in the form of tissues or organs, contact is achieved by immersing the tissues or organs in a solution of the proteins. When the cells are in the form of tissues or organs which contain a vascular system, contact is achieved by perfusing the vascular system with a solution of the proteins, and once perfused, holding the protein solution in the vascular system throughout the period of storage, preservation or exposure to the injurious conditions. Methods of perfusion are well known among those skilled in physiology and surgical procedures.

Cells which can benefit from treatment with the thermal hysteresis proteins in accordance with this invention include cells of a wide variety of types. Examples are oocytes, embryos, leukocytes, erythrocytes, platelets, pancreatic islets, and hepatocytes. Organs which can benefit from the present invention are also widely varied. Examples include the liver, kidney, heart, brain, lung, pancreas, spleen, ovary, and stomach. Tissues which can benefit from the invention include tissues of any of these organs, as well as skin tissue, bone marrow tissue, cornea tissue, and a wide range of others. The invention finds applicability to mammals in general, and will be of particular interest and utility when used in connection with human cells, tissues and organs.

The effect of the thermal hysteresis proteins in inhibiting ion transport across cell membranes extends to a variety of ions, with particular interest to $Ca^{++}$, $K^+$ and $Na^+$ ions, as well as two or more of these ions in combination.

Since excessive ion transport is one physiological effect which accompanies hypothermia, the ability of the thermal hysteresis proteins to inhibit ion transport may be related to the ability of the proteins to enhance cell viability under hypothermic conditions. Accordingly, the amounts and concentrations of protein administered to achieve the effect of inhibition of ion transport are generally the same or similar to the amounts used in enhancing viability under hypothermic exposure.

The ability of the proteins to inhibit ion transport across cell membranes also renders the proteins useful in treating diseases and abnormal physiological conditions in which excessive trans-membrane ion transport is present. Examples of such diseases and conditions are cystic fibrosis, Kartagener's Syndrome, diabetes insipidus, diabetes mellitus, and antidiuretic hormone abnormalities. Administration of the proteins for this effect may be achieved by ingestion, vascular injection, localized application, and various means in general by which other drugs or treatment agents are administered when used in the treatment or management of these diseases and conditions. Again, the concentrations for useful results are generally the same as those referred to above, and the dosage or frequency of administration will be determined by the degree to which the condition being treated has progressed as well as the observed response to the treatment.

Application of the discoveries of the invention also extend to the use of the proteins in the preservation of foods which have a cellular structure. Foods of particular interest for this application are meats and meat products, but other types of foods will benefit as well. For purposes of this invention, meats and meat products include fresh meat and poultry, as well as frozen, canned and dried meats and poultry. Many such foods when cooled to avoid spoilage during transport or storage tend to lose turgor, freshness and other qualities which contribute to their taste, mouthfeel and general appeal. These qualities can be preserved by treatment of the foods with solutions of the proteins in accordance with the present invention. The mode of treatment will vary from one type of food to the next, but will generally involve equilibration of the food with the protein in solution, either by immersion, perfusion, or any other kind of absorption or other means of achieving prolonged contact. The types of solutions and the methods of immersion and perfusion described above in connection with other applications of the invention will be applicable here as well.

The following examples are offered for purposes of illustration, and are not intended to limit the invention in any manner.

Abbreviations used in the examples are as follows:

| AFP | antifreeze polypeptide |
|---|---|
| AFGP | antifreeze glycoprotein |
| ATP | adenosine triphosphate |
| AVS | apparent vitrification solution (composition given in Example 12) |
| BSA | bovine serum albumin |
| EGTA | ethylene glycol-bis($\beta$-aminoethyl ether)N,N,N',N'-tetraacetic acid |
| FCS | fetal calf serum |
| FDA | fluorescein diacetate |
| FSH | follicle-stimulating hormone |
| HCG | human chorionic gonadotropin |
| HEPES | N-2-hydroxyethylpiperazine-N'-2-ethanesulfonic acid |
| HTF | human tubal fluid |
| I.U. | international units |
| LDH | lactate dehydrogenase |
| LTSEM | low-temperature scanning electron microscope (y) |
| PBS | phosphate-buffered saline |
| PMSG | pregnant mare's serum gonadotropin |
| TB | trypan blue |

The sources of AFPs and AFGPs used in these examples were as follows:
Winter flounder: *Pleuronectus americanus* (AFP I)
Ocean pout: *Macrozoarces americanus* (AFP III)
Sea raven: *Hemitripterus americanus* (AFP II)
Antarctic nototheniid: *Dissostichus mawsoni* (AFGP)
Antarctic eel pout: *Austrolycichthys brachycephalus* (AFP III)
The Krebs solution referred to in these examples is a solution having the following composition:

| | |
|---|---|
| $Na^+$ | 327 meq/L |
| $K^+$ | 23 |
| $Ca^{++}$ | 10 |
| $Mg^{++}$ | 2.9 |
| $Cl^-$ | 454 |
| $PO_4^=$ | 11 |
| $SO_4^=$ | 11.4 |
| $HCO_3^-$ (5 vol. %) | Balance |
| pH | 7.4 |

Percentages listed for compositions in the following examples are generally on a volume basis, unless otherwise noted.

EXAMPLE 1

This example illustrates the use of AFPs and AFGPs in the protection of immature bovine oocytes during hypothermic exposure (4° C.). This example is reported in part in Rubinsky, B., et al., *Biochem. Biophys. Res. Comm.* 180(2):566–571 (1991), and in part in Rubinsky, B., et al., *Cryobiology* 28(6): 594 (1991).

The AFPs used in this example were isolated from winter flounder (Type I), ocean pout (Type III) and sea raven (Type II). The AFGPs were isolated from Antarctic nototheniid fish (*Dissostichus mawsoni*). The compositions of the AFPs and AFGPs used in these experiments were the physiological compositions as they naturally occur in the fish from which they were isolated.

Immature bovine oocytes, in multilayered dense cumulus and with no alteration of the cytoplasm, were obtained from selected follicles (2–6 mm) of cow and heifer ovaries brought to the laboratory in warm saline (0.9%). The follicles were aspirated with a 15-gauge needle within 80 minutes of slaughter. The oocytes were kept in PBS supplemented with 0.4% (volume basis) BSA, 0.34 mM pyruvate, 5.5 mM glucose and 15 mM kanamycin. Prior to the hypothermic experiments the oocytes were introduced into Eppendorf vials containing 0.5 mL of the following solutions:

(a) PBS
(b) PBS with 20 mg/mL AFP of Type I (winter flounder)
(c) PBS with 20 mg/mL AFP of Type II (sea raven)
(d) PBS with 20 mg/mL AFP of Type III (ocean pout)
(e) PBS with 20 mg/mL AFGP (nototheniid, (*Dissostichus mawsoni*))

All AFPs and AFGPs had been purified from fish blood plasma using Sephadex G75. The concentration of 20 mg/mL was chosen because it is within the physiological range for all AFPs and AFGPs (the physiological concentration of AFPs is about 20 mg/mL, and the physiological concentration of AFGPs is about 35 mg/mL). Additional control experiments were performed with oocytes in a PBS solution with 0.1M sucrose and in a PBS solution with 20% (volume basis) FCS.

The oocytes were incubated in the various solutions at 4° C. for 24 hours. Upon removal of the oocytes from the 4° C. environment, the integrity of their oolemma was determined using three different tests: morphological examination, fluorescein diacetate (FDA) staining, and trypan blue (TB) exclusion. The morphological examinations were performed using a Leitz microscope with phase contrast.

The FDA staining test is based on the conversion of the FDA to a fluorescent compound, which conversion occurs only when the FDA contacts hydrolases in the live cell. Oocyte viability and oolemma intactness therefore produce intense fluorescence, while the absence of fluorescence indicates a lack of viability. The technique used in this experiment involved exposure of the oocytes to PBS solution containing 5 μg/mL FDA for three minutes. The oocytes were then placed on a slide under a coverslip and screened in a fluorescent microscope (Leitz), to which a photoreceptor capable of qualitatively evaluating the intracellular fluorescence was connected. An oocyte was considered to have an intact oolemma after hypothermic exposure if the quantitative reading of the photoreceptor was within two standard deviations of the mean observed in fresh oocytes.

In the TB exclusion tests, TB exclusion is indicative of an intact oolemma. These tests involved adding an aqueous solution containing 0.1% TB to the PBS solution containing the oocytes, and letting the combined solution stand for 3 minutes. The oocytes were then examined with a phase contrast microscope (Leitz), to determine if the TB was excluded.

Prior to their hypothermic exposure, the fresh oocytes were subjected to the same tests to establish quantitative criteria for use as controls in evaluating the integrity of the oolemma subsequent to hypothermic exposure.

The results of these tests are shown in Table V below.

TABLE V

Hypothermic Exposure Tests on Bovine Oocytes

| Preservation Medium | % of Oocytes With Intact Oolemma After Hypothermic Exposure (n = 20) Test Used: | | |
|---|---|---|---|
| | Morphology | TB | FDA |
| PSB | 10 | 15 | 26 |
| PBS + 20 mg/mL AFP I (winter flounder) | 64 | 70 | 72 |
| PBS + 20 mg/mL AFP III (ocean pout) | 52 | 55 | 75 |
| PBS + 20 mg/mL AFP II (sea raven) | 55 | 65 | 75 |
| PBS + 20 mg/mL AFGP | — | — | 69 (n = 19) |

The data in Table V indicate that only 10% to 26% of the control oocytes retained an intact oolemma following exposure to 4° C. Similar results, not shown in the table, were obtained for oocytes incubated at 4° C. in PBS solution to which 0.1M sucrose or 20% (volume basis) FCS had been added. When either the various AFPs or AFGPs were added to the incubation medium, however, the integrity of the oolemma was retained in 50% to 75% of the oocytes, depending on which test was used to measure the integrity. It is also significant to note that the level of cell membrane protection was similar among the different AFPs and AFGPs despite differences in the primary and secondary structures of the AFPs and between the molecular structures of the AFPs and AFGPs.

Additional tests were performed to determine the ability of the oocytes to undergo in vitro maturation and in vitro fertilization. Following hypothermic exposure (4° C. for 24 hours), the oocytes with their cumulus cells were incubated in a standard maturation medium, TCM-199 with 10% (volume basis) FCS supplemented with 500 mg/mL hormones, LH (NiH-LH-B9) and FSH (bFsH-LER-1596-1) and granulosa cells. The granulosa cells were used at a concentration of approximately $5 \times 10^6$ cells/mL and were obtained by dissection of small, fresh follicles, which were washed and re-collected in the maturation medium. The oocytes were cultured in the incubation medium at 39° C. in an atmosphere of 5% $CO_2$ in air, for 24 hours. After incubation, the oocytes were fixed in an acetic acid/ethyl alcohol mixture (1:3, volume basis) and stained after 24 hours with lacmoid stain to determine the percentage which had undergone in vitro maturation. Microscopic evidence of the second metaphase stage, MII, and/or extrusion of the first polar body were used to determine oocyte meiotic maturation. Incubated oocytes which were not used to study in vitro maturation were fertilized in vitro. Immediately prior to insemination the oocytes were transferred for 5 minutes to a PBS solution containing 0.1% hyaluronidase (Sigma Chemical Company, St. Louis, Mo.) to remove part of the cumulus cells. The oocytes were then placed in a Brackett and Oliphant insemination medium supplemented with 1.9 mg/mL caffeine. Semen frozen in straws was used for in vitro fertilization. After thawing the straws in 35° C. water, the semen was washed by centrifugation in the insemination medium. Capacitation was achieved by incubating the sperm for 15 minutes in the insemination medium supplemented with heparin (100 mg/mL). Capacitated bull sperm at a final concentration of $10^6$ cells/mL were then coincubated with in vitro matured oocytes. After 14–16 hours of culture, the oocytes were fixed and stained, and oocyte morphology (cytoplasm, oolemma) and fertilization were evaluated.

The results of these tests are shown in Table VI below, which includes comparative results from tests involving hypothermic incubation in PBS without AFPs ("PBS Alone"), as well as from tests involving no hypothermic exposure at all ("Fresh Oocytes"). The ratios shown in this table represent the number of oocytes which have successfuly undergone either in vitro maturation of in vitro fertilization vs. ("/") the total number of oocytes used in each experiment. The ratios are also expressed as percentages in the parentheses.

TABLE VI

In Vitro Maturation and Fertilization Tests On Bovine Oocytes

| Incubation Medium | Proportions Matured or Fertilized | |
|---|---|---|
| | Maturation | Fertilization |
| PBS Alone | 16/68 (23.5%) | 0/33 (0%) |
| PBS + 20 mg/mL AFP I (winter flounder) | 44/62 (71%) | 14/32 (43.75%) |
| PBS + 20 mg/mL AFP III (ocean pout) | 38/52 (73.1%) | 12/25 (48%) |
| PBS + 20 mg/mL AFP II (sea raven) | 41/62 (66.1%) | 12/32 (37.5%) |
| PBS + 20 mg/mL AFGP | 16/25 (64%) | 12/25 (48%) |
| Fresh Oocytes | 16/20 (80%) | 15/27 (55.6%) |

The maturation tests indicate that while only 23.5% of the oocytes incubated under hypothermic conditions in PBS alone underwent in vitro maturation, 64% to 75% matured when exposed to the same conditions in the presence of AFPs and AFGPs, comparing well with the percentage for fresh oocytes (80%). By contrast, when 0.1M sucrose or 20% (volume basis) FCS was substituted for the AFPs, the maturation rate was only about 30% (this data is not included in the table).

The fertilization tests indicate that none of the "PBS Alone" oocytes underwent in vitro fertilization, whereas 40–50% of the oocytes incubated in the presence of AFPs or AFGPs were fertilized. Thus, all AFPs and AFGPs tested were shown to have a similar effect. This rate of fertilization is comparable to that obtained for immature oocytes under normal conditions (approximately 60%). These results demonstrate that all the known types of AFPs and AFGPs are similarly effective in (a) preserving the integrity of the cell membrane, and (b) preserving the functional viability of cells, both during hypothermic exposure.

EXAMPLE 2

This example illustrates the use of AFPs in the preservation of human oocytes during exposure to hypothermic conditions. The AFPs used were isolated from winter flounder (Type I) and ocean pout (Type III).

The oocyte donor was a 27-year-old woman with primary infertility due to combined diagnosis of chronic anovulation and male factor infertility. While the donor had undergone three previous attempts at in vitro fertilization using a standard procedure which yielded a fertilization rate of 5.7%, no attempts had been made using subzonal sperm insertion. The donor was stimulated with a combination of FSH and human menopausal gonadotropins. Transvaginal oocyte retrieval was performed 37 hours after the stimulation with human menopausal gonadotropins, yielding 32 oocytes. In addition, two semen samples, both azoospermic, were collected from the husband of the oocyte donor.

After retrieval, the oocytes were placed in human tubal fluid (HTF) (Irvine Scientific, Irvine, Calif.) supplemented with 10% heat-inactivated fetal human cord serum (insemination medium), and maintained at 37° C. in a gas mixture of 5% $CO_2$ and 95% air. Within two hours, the oocyte-cumulus complexes were exposed to hyaluronidase (Fisons, Ovine, United Kingdom) at a concentration of 700 I.U./mL dissolved in HTF, in preparation for microinjection of sperm. After 2 minutes, the oocytes were pipetted several times and removed from the hyaluronidase, rinsed twice in fresh HTF, placed in fresh insemination medium, and returned to the incubator to reequilibrate for at least 20 minutes. Remaining corona radiata cells were removed by gentle aspiration through a finely pulled capillary pipette. Each oocyte was evaluated in terms of its shape and the condition of its ooplasm and for the presence of a polar body or germinal vesicle. The oocytes were then returned to the incubator to reequilibrate for approximately 1 hour. Three oocytes were atretic and were therefore not included in the study.

For hypothermic exposure, the oocytes were divided into groups and each group placed in a single cryotube, each cryotube containing one of the following solutions:

(a) 1 mL of PBS alone (modified Dulbecco's Phosphate Buffered Saline, Sigma Chemical Company, St. Louis, Mo., supplemented with 10% fetal human cord serum) (number of oocytes n=8)

(b) 1 mL of PBS containing 1 mg/mL AFPs from ocean pout (n=5)

(c) 1 mL of PBS containing 10 mg/mL AFPs from ocean pout (n=5)

(d) 1 mL of PBS containing 1 mg/mL AFPs from winter flounder (n=5)

(e) 1 mL of PBS containing 10 mg/mL AFPs from winter flounder (n=6)

In the various cryotubes, the oocytes were exposed to 4° C. for twenty hours. After this exposure, the cryotubes were permitted to warm to room temperature, and the oocytes were removed from each cryotube, rinsed twice in fresh insemination medium, and placed in culture at 37° C. in 5% $CO_2$. The oocytes were then allowed to equilibrate for four hours.

To test for insemination and embryo culture, a fresh semen specimen was obtained and prepared by washing two times in insemination medium, followed by resuspension and fall-down. After fifteen minutes, the upper layer was removed from the suspension, and the concentration of motile sperm determined. The oocytes were then inseminated with a final concentration of $1 \times 10^6$ motile sperm/mL.

Thirty-eight hours after insemination, embryos resulting from monospermic fertilization were assessed for the number and morphology of the embryos, and the results are shown in Table VII.

TABLE VII

Cleavage and Morphology of Embryos Derived from Monospermic Fertilization of Human Oocytes After Hypothermic Exposure at 4° C.

| Immersion Solution During Exposure | No. of Inseminated Oocytes | No. of Cleaved Embryos | Embryo No. | Morphology | | | |
|---|---|---|---|---|---|---|---|
| | | | | No. of Blastomeres | Shape | Cytoplasm | Fragments |
| PBS alone | 8 | 2 | #1 | 2 | unequal | even | ++ |
| | | | #2 | 2 | unequal | even | ++ |
| Ocean pout: 1 mg/mL | 5 | 3 | #1 | 2 | equal | even | + |
| | | | #2 | 3 | equal | even | + |
| | | | #3 | 2 | equal | even | + |
| Ocean pout: 10 mg/mL | 5 | 0 | | | | | |
| Winter flounder: 1 mg/mL | 5 | 3 | #1 | 2 | equal | even | + |
| | | | #2 | 2 | equal | even | + |
| | | | #3 | 2 | unequal | even | ++ |
| Winter flounder: 10 mg/mL | 6 | 1 | #1 | 2 | unequal | dark | + |

To summarize these results, among the eight control oocytes, only two embryos were obtained, and each of these was of a low grade. Among the ten oocytes which comprised the two groups preserved with AFPs at 1 mg/mL, six 2- to 3-cell stage embryos resulted, five of these with regular blastomeres and even cytoplasm. Of the eleven oocytes which comprised the two groups preserved with AFPs at 10 mg/mL, only one embryo was derived, and that embryo was of a low grade. This confirms that the AFPs are useful in protecting human oocytes as well as bovine oocytes, although their protective effect on human oocytes is best seen at low concentrations.

EXAMPLE 3

This example illustrates the use of AFPs in improving the integrity and viability of whole mammalian organs stored at hypothermic temperatures. This example is reported in Lee, C. Y., et al., Cryo-Letters 13:59–66 (1992).

The AFPs used in this study were isolated from Newfoundland ocean pout (AFP III), and consisted of a family of at least ten independently active polypeptides with molecular weights ranging from 6,000 to 7,000. The AFP composition used in this study was the same as the physiological composition naturally occurring in the fish from which the AFPs were isolated. The mammalian organs used in this study were livers removed from Sprague-Dawley rats, ages 50–55 days. The studies involved perfusing the livers with a test solution and storing them at hypothermic temperature, then assessing their viability by testing them for lactate dehydrogenase (LDH) release into the perfusate and for bile production. These tests are recognized in the art as the most consistent and reliable in vitro indicators of liver viability.

The livers were prepared as follows. With the rats placed under nembutal anesthesia, the livers were exposed by longitudinal midline and transverse subcostal incisions. The bile duct of each liver was then cannulated with a PE-10 polyethylene catheter and bile was collected for ten minutes while surgery proceeded. After partial mobilization of the liver from the adjacent tissue, a 16-gauge Teflon ® intravenous catheter attached to a syringe containing 1,000 units of heparin in 3.0 mL of saline was introduced into the portal vein and the saline was rapidly infused. The inferior vena cava was then ligated above the renal vein and freed from the adjacent peritoneal tissue. A PE-205 polyethylene catheter was secured in the inferior vena cava through an incision in the right atrium. The entire liver was then carefully dissected and washed with warm Krebs buffer solution (Sigma Chemical Company, St. Louis, Mo., USA). For the remainder of the surgical procedure, the portal vein catheter was infused with the Krebs solution pre-equilibrated with a 95:5 mixture of $O_2$ and $CO_2$ at 38° C.

The livers, which weighed between 7 and 10 grams each, were segregated into three groups of four to six livers each. The livers of the first group were perfused with a 2.5 mL filtered solution of Krebs buffer containing 15 mg/mL AFP, injected through the catheter. The 15 mg/mL level was chosen because it is within the physiological range in the fish from which the AFP was taken, at the lower end of the range. In the second and third groups, the perfusate was a 2.5 mL of Krebs solution without the AFP. The first and second groups were placed in hypothermic storage at 4° C. for 24 hours.

After the hypothermic storage of the first and second groups, the livers of all three groups were flushed with 20 mL of Krebs solution at ambient temperature, then immediately connected to a single-pass gravity-driven perfusion circuit via the portal vein catheter. The perfusate was a Krebs solution maintained at 38° C., pre-equilibrated with a 95:5 mixture of $O_2$ and $CO_2$. The flow rate was initially set at 5 mL/min, then increased to 25 mL/min. Perfusion was continued at 25 mL/min for 45 minutes and the effluent was continuously collected in individual vials for the intervals 0–5 minutes, 5–10 minutes, 10–25 minutes and 25–45 minutes following removal from hypothermic storage. LDH activity was measured in the vials with effluent samples using a standard colorimetric technique (Sigma Diagnostics, LDH Kit 500; Shimadzu UV-160A Recording Spectrophotometer). Bile flow commenced 3–5 minutes after the single pass perfusion was initiated. Bile from the cannulated bile duct was collected continuously in vials in consecutive 15-minute intervals.

The levels of LDH activity measured in the effluent samples reached a maximum during the first two collection intervals. The values then decreased and achieved stable levels during the last two intervals. Measurements taken during the third period represented a measurement of the irreversible damage inflicted upon the hepatocytes during hypothermic storage and provided the most consistent results. According to these measurements, LDH activity in the perfusate for the AFP-perfused group (i.e., the first group) was 158±103 Berger-Broida ("B-B") units/mL (averaged over four livers), whereas LDH activity in the perfusate for the group not perfused with AFP (i.e., the second group) was 655±280 B-B units/mL (averaged over six livers). The corresponding figure for the third group (livers not subjected to hypothermic storage) was 70±28 B-B units/mL (averaged over five livers). The use of B-B units is known in the art, as referenced by Cabaud, P. G., et al., *Am. J. Clin. Pathol.* 30:234 (1958).

In summary, the LDH activity levels in the perfusates of livers stored at 4° C. in the AFP solution were considerably lower than (less than 25% of) the levels in the perfusates of livers similarly stored but in the absence of AFP. These figures indicate that the AFP protected the hepatic cell membrane from damage during hypothermic exposure.

Bile production measurements indicated that a plateau was reached during the second 15-minute collection period, with production levels remaining at that plateau for the remainder of the experiment. For the first group of livers (hypothermic storage with AFP protection), the plateau level was 0.5±0.27 mL/h per 100 g of liver (averaged over six livers). For the second group (hypothermic storage without AFP protection), the plateau level was 1.53±0.35 mL/h per 100 g of liver (averaged over four livers). The corresponding figure for the third group (livers not subjected to hypothermic storage) was 2.9±0.4 mL/h per 100 g of liver (averaged over five livers). Clearly, the presence of the AFP in the perfusate during hypothermic storage resulted in a significant improvement of bile flow when compared to livers similarly treated except for the absence of the AFP. Increased bile production observed for livers treated with AFP is a strong indication that these proteins can help to maintain the function integrity of the liver during hypothermic storage.

EXAMPLE 4

This example further illustrates the storage of whole mammalian organs at hypothermic temperatures, except that AFGPs are used in place of AFPs. The organs here as well were livers from Sprague-Dawley rats, ages 50–55 days. The AFGPs used were obtained from Antarctic nototheniid fish (*Dissostichus mawsoni*), and included the full range of fractions 1–8 at a total concentration of 20 mg/mL, in the physiological composition in which they are found in the fish.

The livers were prepared as follows. With the rats placed under nembutal anesthesia, the peritoneal cavity was entered, the bile duct of each liver was cannulated with a PE-30 polyethylene catheter, and bile was collected for ten minutes while surgery proceeded. After partial mobilization of the liver from the adjacent tissue, a 16-gauge Teflon ® intravenous catheter attached to a syringe containing 1,000 units of heparin in 3.0 mL of perfusion buffer was introduced into the portal vein and rapidly infused. The inferior vena cava was then transected distally and the portal vein catheter was infused with Krebs solution pre-equilibrated with a 95:5 mixture of $O_2$ and $CO_2$ at 0° C. This infusion continued for the remainder of the procedure. The inferior vena cava was ligated above the renal vein and freed from the adjacent peritoneal tissue. A PE-205 polyethylene catheter was secured in the superior vena cava through an incision in the right atrium, and samples of the effluent were collected. The entire liver was then carefully dissected and washed with warm saline. For the remainder of the surgical procedure, the portal vein catheter was infused with the Krebs solution pre-equilibrated with a 95:5 mixture of $O_2$ and $CO_2$ at 38° C.

For the test livers, the perfusion line was removed and a 3 mL solution of Krebs solution containing 20 mg/mL of the AFGPs was injected into the catheter. Each liver was then immediately placed in a container filled with cold Krebs solution, and the container with the liver inside were placed in a constant temperature apparatus, where the temperature of the liver and the Krebs solution were maintained constant at 4° C. Livers were stored in this manner for periods of 6, 12, and 24 hours.

After storage, the livers were removed and injected with 3 mL of Krebs solution at ambient temperature to remove the AFGP solution. Each liver was then immediately inserted in a single-pass perfusion circuit where the liver was infused with a Krebs solution pre-equilibrated at 37° C. with a 95:5 mixture of $O_2$ and $CO_2$. The flow rate was initially set at 5 mL/min, then increased to 25 mL/min, with careful attention to the position of the liver and catheter. Perfusion was continued at 25 mL/min for 45 minutes and the effluent was continuously collected in individual vials for the intervals 0–5 minutes, 5–10 minutes, 10–25 minutes and 25–45 minutes. Bile was collected in fifteen-minute intervals.

To serve as controls, fresh livers were injected with 3 mL of Krebs solution at ambient temperature. The procedure of the last paragraph was then followed except that AFGP addition was omitted. The livers were then immediately inserted in the single-pass perfusion circuit, and effluent and bile samples were taken as described above.

Bile and LDH measurements were taken in the same manner described in the preceding example. The results are shown in Tables VIII and IX below.

TABLE VIII

Bile Production Tests on Rat Livers

| Time of Exposure to 4° C. (hours) | Bile Production (mL/100 mg/hour) Treatment Solution: | |
|---|---|---|
| | Krebs alone | Krebs + AFGP |
| 0 | 3.0 ± 0.5 | 3.0 ± 0.5 |
| 6 | 1.7 ± 0.5 | 2.5 ± 0.35 |
| 12 | 1.0 ± 0.25 | 1.75 ± 0.55 |
| 24 | 0.38 ± 0.28 | 1.0 ± 0.3 |

TABLE IX

LDH Activity Tests on Rat Livers

| Time After Onset of Perfusion (min) | LDH Activity (B-B units/mL) Protocol: | | |
|---|---|---|---|
| | Krebs alone; no storage | Krebs + AFGP; 24 h storage at 4° C. | Krebs alone; 24 h storage at 4° C. |
| 0–5 | 50 ± 30 | 970 ± 200 | 1110 ± 60 |
| 5–10 | 50 ± 15 | 280 ± 210 | 820 ± 290 |
| 10–25 | 60 ± 40 | 250 ± 210 | 790 ± 280 |

Table VIII shows that there is a significant increase in bile production from livers stored with AFGPs for all storage times tested, which illustrates that the AFGPs preserve the functional integrity of whole organs during hypothermic storage. The LDH activity tests in Table IX also show the benefit achieved by the presence of AFGPs, indicating that the AFGPs protected the hepatic cell membranes during storage under hypothermic conditions.

EXAMPLE 5

This example further illustrates the use of AFGPs in improving the integrity and viability of whole mammalian organs stored at hypothermic temperatures. The AFGPs used in this study were obtained from Antarctic nototheniid (*Dissostichus mawsoni*) used in the composition in which they naturally occur in the fish, and the organs were adult rabbit hearts.

Two white laboratory rabbits weighing 2–3 kg each were anesthetized, and the heart was surgically removed from each. One heart, serving as a control, was perfused with Krebs solution for 30 seconds at 5° C., after which time 5 mL of standard Krebs solution at 5° C. were injected into the aorta chamber. The second heart was perfused and injected in the same manner except that the Krebs solution contained 20 mg/mL of the AFGPs. Each heart was then immediately placed in a small test tube containing Krebs solution at 5° C., and the tubes were placed in an ice/water bath at 0° C.

Both hearts were held at 0° C. for 4 hours, then connected to a Langendorf perfusion system, where they were perfused with Krebs solution at 37° C. for one hour. During this time, the aorta in the first heart beat weakly. At the end of the hour, the aortic pressure in the first heart was about 27 mm of water, aortic flow was negligible, and the flow rate through the heart was about 2 cc/min. The heart was non-vigorous, beating at a rate of about 30 beats per minute. Upon visual observation, portions of the heart tissue appeared to be dead or dying.

The behavior of the second heart was distinct from the first. At the end of the hour of perfusion at 37° C., the aortic pressure was over 100 mm of water, aortic flow was 12 cc/min, and the cardiovascular flow rate was about 47 co/min. This heart was vigorous, beating about 160 beats per minute. These values are close to those of a normal adult rabbit heart. Visually, the heart looked robust.

EXAMPLE 6

This example, reported in pan by Rubinsky, B., et al., *Biochem. Biophys. Res. Comm.* 1173(5): 1369–1374 (1990), illustrates the ability of AFGPs to protect cell membranes and membrane function at hypothermic temperatures. Through measurements of the resting potential and in vitro culture of pig oocytes, the experiments reported in this example demonstrate that AFGPs protect the structural integrity of the oolemma and its function following exposure to hypothermia. Microscopic observations of the oocytes and their oolemma not included in the publication are added at the end of this example to confirm the results of the resting potential tests.

The oocytes used were immature pig oocytes surrounded by the cumulus, obtained from selected follicles of cyclic sows 20 minutes after slaughter, at 20° C. The AFGPs were obtained from Antarctic nototheniid (*Dissostichus mawsoni*). To isolate the AFGPs in fractions for this example, blood serum containing the AFGPs was chromatographed into various fractions on a Sephadex G75 column in 0.1M $NH_4HCO_3$. The antifreeze activity (thermal hysteresis) of each fraction was measured using a Clifton nanoliter osmometer. Active fractions were pooled, lyophilized, and rechromatographed on Sephadex G75. Pooled combinations of fractions 1–8 and separately 1–5 and 7–8 were prepared in this manner.

The oocytes were placed in vials containing different concentrations and combinations of AFGPs in PBS supplemented with 0.4 w/v BSA, 0.34 mM pyruvate, 5.5 mM glucose and 70 μmol/mL kanamycin. To determine the protective effect of the AFGPs the oocytes were exposed for either 4 hours or 24 hours to a temperature of 4° C. in a constant temperature chamber.

After removing the oocytes from the 4° C. environment, the integrity of the oolemma was determined by measuring the resting membrane potential of the oocytes at room temperature (22° C.). Intracellular voltage measurements were made using single microelectrodes made from borosilicate glass tubes. The electrodes were pulled on a horizontal puller and filled with 2M KCl. The resistance of the electrodes was 10–20 megaohms. To record the membrane potential, the tip of the microelectrode was maneuvered to the surface of the cell using a micromanipulator controlled by observation under a Leitz Fluovert microscope equipped with Nomarski optics with a magnification of 400×. When the tip just dimpled the surface of the cell, the final penetration was achieved by briefly causing an electrical oscillation induced by turning the capacity compensation of the amplifier. The electrical potential values, which remained constant for at least 1–2 minutes, were recorded. The resting membrane potential is a very sensitive criterion for functional integrity of the membrane, as well as a direct measure of ion leakage through the membrane.

The results of the resting potential measurements are shown in Table X below. Each entry in the table is a ratio of the number of oocytes with a normal resting potential following exposure to hypothermic conditions to the total number of oocytes exposed. To establish a criterion for the normal potential, preliminary experiments were performed for each batch of oocytes in which the membrane potential of fresh oocytes was measured at 22° C. The mean value of the electric potential $\bar{u}$ and the standard deviation $\sigma$ were calculated for each batch. The mean and the standard deviation were measured in fresh oocytes in PBS solution and in a PBS solution with 40 mg/mL AFGPs. Comparison of the results showed that the AFGPs had no effect on the resting potential of fresh oocytes. For the test measurements involving exposure to hypothermic conditions, an oocyte was considered to have a normal membrane potential if the absolute value of the resting potential measured at 22° C. after hypothermic exposure was higher than the absolute value of either $|\bar{u}|-|\sigma|$ or $|\bar{u}|-|2\sigma|$. The first criterion is the more stringent of the two and being identified in the table as Criterion A, and the second is identified as Criterion B. The mean of all means for $\bar{u}$ was −31 mv, and the mean standard deviation was 4.5 mv. These values are within the normal range of membrane potentials for pig oocytes.

TABLE X

| Composition of Solution | Oolemma Resting Potential Ratios of Normal to Total Tested | | | |
|---|---|---|---|---|
| | Exposure Time at 4° C.: | | | |
| | 4 h | 4 h | 24 h | 24 h |
| | Criterion Used for "Normal": | | | |
| | A | B | A | B |
| PBS | 6/48 (12.5%) | 9/48 (18.8%) | 0/17 (0%) | 0/17 (0%) |
| PBS + 0.1 mg/mL AFGP 1-8 | 7/29 (24%) | 11/29 (37%) | 0/14 (0%) | 0/14 (0%) |
| PBS + 1 mg/mL AFGP 1-8 | 19/27 (70%) | 20/27 (74%) | 6/14 (42%) | 9/14 (64%) |
| PBS + 40 mg/mL AFGP 1-8 | 54/70 (77%) | 59/70 (84%) | 7/17 (41%) | 9/17 (53%) |
| PBS + 40 mg/mL AFGP 1-5 | 12/43 (28%) | 21/43 (48%) | 0/14 (0%) | 0/14 (0%) |
| PBS + 40 mg/mL AFGP 7,8 | 11/47 (23%) | 18/47 (38%) | 0/14 (0%) | 0/14 (0%) |

The data in Table X show that after 4 hours of exposure at 4° C., the membrane potential of between 87.5% and 81.2% of the oocytes preserved in a PBS solution dropped below one and two standard deviations, respectively, of the normal value of the membrane potential of fresh oocytes. In contrast, from 70% to 84% of the oocytes exposed to the same time and temperature conditions but in PBS with AFGPs retained a normal resting potential. The protection afforded by AFGPs 1–8 was consistently high at all concentrations ranging from 40 mg/mL down to 1 mg/mL, below which the protection drops to low values at 0.1 mg/mL AFGP 1–8. The data further show that while the AFGPs when used in the full physiological composition gave the most effective results, all AFGP compositions tests provided some degree of protection. Still further, the data show that after 24 hours of exposure, a highly significant percentage of oocytes retained a normal membrane potential (ranging from 41% and 64%) with 40 mg/mL AFGP to 1 mg/mL AFGP, whereas none of the oocytes in PBS or PBS with 0.1 mg/mL AFGP 1–8 had a measurable resting potential. In summary, the resting potential across the oolemma upon exposure to hypothermic conditions in the absence of AFGPs dropped rapidly, indicating membrane damage and ion leakage, whereas much less of a drop occurred when exposure was done in the presence of AFGPs.

Experiments were also performed by observation under a microscope to determine the viability of the oocytes and the morphological integrity of the oolemma following exposure to the hypothermic conditions. Oocytes were exposed to 4° C. for 4 hours, in solutions of PBS and PBS with 40 mg/mL AFGP 1–8. After hypothermic exposure, the oocytes were incubated in TCM-199 solution supplemented with 10% FCS, 5 μg/mL sheep luteinizing hormone (NIH S20), pig follicle stimulating hormone (LER 441-2) and 20 ng/mL of pig prolactin (LER 2073), at 37° C. under 5% $CO_2$ for 44 hours. After incubation the oocytes were fixed in acetic acid/ethyl alcohol (1:3, volume basis) and stained by lacmoid stain. The viability of the immature pig oocytes was assessed using phase contrast microscopy by their ability to develop in vitro from the initial germinal vesicular stage to the first metaphase MI or second metaphase MII, and to present a normal morphology, i.e., cytoplasmatic compactness, intact oolemma, visible nuclear stage. The microscope observations also provided a qualitative evaluation of the structural integrity of the oolemma.

The microscope observations indicated that in the absence of AFGPs, only 2 of 20 oocytes retained a morphologically intact oolemma, and none of the oocytes matured in vitro. In contrast, when 40 mg/mL AFGPs were present, 11 of the 18 oocytes retained a morphologically intact oolemma, and 4 of the 18 underwent in vitro maturation.

EXAMPLE 7

This example illustrates the ability of AFPs and AFGPs to block ion channels in mammalian cells. The AFPs used in this example were isolated from winter flounder (AFP I), the AFGPs were isolated from Antarctic nototheniid (*Dissostichus mawsoni*), and the mammalian cells were porcine granulosa cells. This example is reported in part in Rubinsky, B., et al., *Am. J. Physiol.* 262 (*Regulatory Integrative Comp. Physiol.* 31):R542–R545 (1992).

Pig granulosa cells were harvested from healthy antral follicles, 3 to 6 mm in diameter, obtained from pig ovaries collected immediately after slaughter. The cells were washed twice in PBS supplemented with 0.4% (volume basis) BSA, 0.34 mM pyruvate, 5.5 mM glucose and 14 mM kanamycin, and resuspended in a recording solution containing 130 mM NaCl, 3 mM KCl, 10 mM $CaCl_2$, and 10 mM HEPES at pH 7.2. Recording was carried out using a patch-clamp technique in the whole cell configuration. The electrodes were made of borosilicate glass using a horizontal puller and had an outside diameter of 1–2 microns and a resistance of 5 to 20 $M\Omega$ when dipped into the bath solution. The whole cell electrode solution contained 140 mM KCl, 1 mM EGTA and 10 mM HEPES. A List EPC7 amplifier was used to measure the cell current and an ITC16 interface connected to an Atari Mega 4 computer and a software program entitled Patch Program Instrutech were used to store and analyze the data.

The experiments were performed at room temperature (22° C.). the procedure involved introducing the granulosa cells into 100-$\mu$L droplets under the microscope and eliciting currents using 200-ms depolarizing pulses from $-80$ mV to $-30$ mV for the calcium current and 1000-ms depolarizing pulses from $-40$ mV to $+60$ mV for the potassium current. After the normal currents were established and recorded, the AFPs and AFGPs in boluses of 5 $\mu$L were injected into the 100-$\mu$L droplets individually using a micromanipulator. The concentrations of the AFPs and AFGPs in the boluses were set to achieve concentrations of 0.1 mg/mL, 0.5 mg/mL, 1 mg/mL, 5 mg/mL, 10 mg/mL and 20 mg/mL in the droplets. The time of the injection of each bolus was coordinated with the current reading to generate complete current records at the instant of the injection and every 20 seconds thereafter.

Separate experiments were performed for the $K^+$ and $Ca^{+2}$ currents. At least three experiments were performed for each of the AFP and AFGP concentrations listed above. Negative control experiments were also performed in 100-$\mu$L droplets with 0.1M BSA and 0.1M soybean trypsin inhibitor.

Current measurements taken in the absence of AFPs and AFGPs showed behavior in accordance with known channel kinetics. For the $Ca^{+2}$ current tests, the behavior was typical of T-type $Ca^{+2}$ channel kinetics, the depolarization pulse producing an initial rapid activation phase followed by an inactivation phase. For the $K^+$ current tests, the behavior had the characteristics typical of a delayed rectifier, with the depolarization pulse causing a slow, delayed activation phase rising to a plateau, with no subsequent inactivation during the pulse.

In the experiments where BSA and soybean trypsin inhibitor were included in the droplets, current measurements compared with those taken in the absence of these additives showed that neither of these additives had any effect on the ion currents.

Current measurements taken in the presence of AFPs and AFGPs gave results as follows. In both the $Ca^{+2}$ and $K^+$ measurements, the ion currents remained unchanged throughout the entire five-minute duration of the tests at AFP and AFGP concentrations of 0.1 mg/mL (0.028 mM), indicating that at this concentration neither the AFPs nor the AFGPs had any effect on the ion currents during this time period and at the measurement resolution achieved in these experiments. At concentrations of 0.5 mg/mL (0.14 mM) or higher, however, the tests consistently showed inhibition of the ion currents. In the $Ca^{+2}$ current tests, the current achieved in the presence of 1.0 mg/mL AFPs and in the presence of 0.5 mg/mL AFGPs was of a reduced magnitude 20 seconds after the AFPs or AFGPs were introduced, and completely suppressed after 40 seconds. In the $K^+$ current tests, the currents achieved in the presence of 1 mg/mL (0.28 mM) AFPs and in the presence of 1 mg/mL (0.28 mM) AFGPs were completely suppressed within 400 seconds, while the currents achieved in the presence of 10 mg/mL (2.8 mM) AFPs or 10 mg/mL (2.8 mM) AFGPs were completely suppressed within 20 seconds. Higher concentrations of AFPs and AFGPs resulted in still faster suppression of both types of ion currents. In general, the effect on the $Ca^{+2}$ current was greater than on the $K^+$ current.

EXAMPLE 8

This example further illustrates the ability of AFPs to block ion channels in mammalian cells. This example is reported in Negulescu, P. A., et al., *Am. J. Physiol.* 263 (*Cell Physiol.* 32): PC1310-3 (December 1992). The AFPs used in this example were isolated from Newfoundland ocean pout (AFP III) and used in their physiological composition, and the cells were parietal cells from rabbit gastric glands.

To form intact rabbit gastric glands, minced gastric mucosa from New Zealand white rabbits was placed in a digestion medium that contained 0.3 mg/mL type 1A collagenase in an Eagle's minimum essential medium (GIBCO), supplemented with 1 mg/mL BSA (Calbiochem), $10^{-4}M$ cimetidine (a histamine H2 blocker to insure that the glands remained unstimulated), and 20 mM HEPES. The solution was stirred and gassed with 100% oxygen gas at 37° C. Glands were formed within 45 minutes. These glands were allowed to settle and were then rinsed several times at room temperature in Eagle's medium (Sigma Chemical Company, St. Louis, Mo., USA) containing 40 $\mu$M cimetidine without enzymes or albumin. This procedure is taken from Berglindh, T., et al., *Acta. Physiol. Scand.* 96:150–159 (1976).

For measurements of intracellular free calcium ($Ca_i$), a suspension of isolated gastric glands (5% cytocrit) was loaded with fura-2/AM, a calcium-sensitive fluorescent indicator in Eagle's medium containing $10^{-4}M$ cimetidine and 10 $\mu$M dye for thirty minutes at 24° C. Following loading, the glands were washed in Eagle's medium and left at room temperature until use.

The fluorescence measurements in each cell were calibrated using the formula derived by Grynkiewicz, G., et al., *J. Biol. Chem.* 260:3440–3450 (1985) for dual wavelength measurements:

$$Ca_i = K \times \frac{(R - R_{min})}{(R_{max} - R)}$$

where $R_{min}$ is the ratio of fluorescence intensities at 340 nm and 385 nm obtained at zero Ca, $R_{max}$ is the ratio at saturating Ca, and R is the measured ratio. The values of $R_{min}$, $R_{max}$ and K were determined in separate experiments, by the method of Negulescu, P. A., *Methods Enzymol.* 192:38-77 (1990).

Gastric glands loaded with fura-2 were mounted in a perfusion chamber and placed over the objective (40×) of a Zeiss IM35 inverted microscope at 37° C. Fluorescence from single cells within intact gastric glands was measured using digital image processing of video images of the fluorescence of each excitation wavelength. Black and white fluorescence images of whole glands were acquired using a Silicon Intensified Target Camera and relayed to a Gould FD5000 image processor which was controlled by a DEC computer (PDP 11/73). After correcting for background and dark current of the camera, the fluorescence intensity ratio was calculated for each pixel and displayed as one of 32 pseudocolors. These ratios were then calibrated. Analysis and plotting of ratio vs. time for the individual cells was accomplished using a graphics emulation terminal (Smarterm 240) which allowed for the collection of data from individual parietal cells. Acid-secreting parietal cells were easily distinguished from neighboring enzyme-secreting chief cells by visual observation. Parietal cells were chosen because they demonstrate larger plateau responses of $Ca_i$ than do the chief cells.

All experimental solutions contained the following:

| | |
|---|---|
| NaCl | 144.0 mM |
| K$_2$HPO$_4$ | 2.0 mM |
| CaCl$_2$ | 2.0 mM |
| MgSO$_4$ | 1.0 mM |
| glucose | 11.0 mM |
| HEPES | 10.0 mM |
| pH | 7.45 |

The parietal cells were repeatedly stimulated with 100 μM carbachol. A trace representing the average $Ca_i$ signal from ten parietal cells in one gastric gland vs. time showed a biphasic increase of $Ca_i$ for each stimulation, each increase consisting of a rapid initial rise (or spike) followed by a plateau at mid-height before returning to the baseline level. The spike is caused by the released of Ca from internal stores and the decay is caused by ATP ion pumps pushing Ca ions out of the cells, while the plateau is generated by the balance between the ATP ion pumps and the entry of Ca ions from the extracellular space through ion channels into the cells. The carbachol completely empties the intracellular pool, while the plateau phase, which is stable for up to 50 minutes, requires the presence of extracellular Ca. Otherwise, the $Ca_i$ would return immediately to the baseline. During the plateau phase, the rate of Ca entry into the cells from the extracellular space is increased relative to the resting condition, and, since the cell is in a new steady state during the plateau, there is also an increased pumping of Ca out of the cell during this time.

The nature and regulation of the channels that control this entry into parietal and other types of epithelial cells are not well understood. The channels appear to be different from those in excitable tissues because they are not blocked by either nifedipine or verapamil, though they are, like other Ca channels, inhibited by 50 μM La and low pH of less than 6.7. The trace indicated that the characteristic profile of each phase is maintained through multiple stimulations, indicating that cells are able to refill their intracellular stores relatively quickly and that desensifization of the response does not occur under control conditions.

To test the effect of AFPs, dose-response studies were performed with concentrations of AFPs ranging from 0.1 mg/mL to 20 mg/mL. No effect on Ca transport was observed at 0.1 mL, while complete blocking of the carbachol-induced plateau was achieved at concentrations of 1 mg/mL (140 μM) and above. At 1 mg/mL, the AFPs had no effect on the carbachol-induced $Ca_i$ spike. Since the spike requires carbachol/receptor binding, phospholipase C activation, and IP3 formation, this indicates that the AFPs had no inhibitory effect on any of these biochemical pathways. In addition, when the cells were stimulated with Ca-free solutions, the rate of decrease of $Ca_i$ following the spike was the same in both AFP-treated and control cells, indicating that the AFPs also had no effect on the Ca-ATPase in the plasma membrane which rids the cells of the released Ca. Thus, the action of 1 mg/mL in blocking the secondary plateau phase of the carbachol response suggests that this protein acts selectively to inhibit the influx of Ca.

Since influx of extracellular Ca is normally required for refilling of intracellular cell pools, a test was conducted to determine whether the AFPs blocked the influx sufficiently to prevent repetitive carbachol stimulations from causing repetitive increases in $Ca_i$. For this test, cells were stimulated with AFP-containing solution for 3 minutes before the carbachol stimulation. The cells were then stimulated three times with carbachol, once in control condition and two more times in the presence of the AFPs. Based on an average of ten cells from one gastric gland, the AFPs eliminated the plateau and also prevented the refilling of the internal store, because the second stimulation of the cells in the presence of the AFPs was blocked. The continued presence of AFPs prevented a third carbachol stimulus from causing a normal release of Ca from the pool, which strongly suggests that prolonged AFP treatment blocked the refilling of the pool, an effect which is similar to the effect of La. Thus, in the presence of 1 mg/mL, only one stimulus is possible.

In a test involving a short-term treatment with the AFPs, the cells were stimulated four times with carbachol, the first time without the inclusion of the AFPs, the second time with the inclusion of the AFPs, and the third and fourth without. The AFPs were washed out between the third and fourth stimulations. The trace of $Ca_i$ vs. time showed that the effect of the AFP was to block the plateau. The effect of the third and fourth stimulations was to partially refill the internal stores, since the heights of the third and fourth spikes were approximately 60% of the height of the second. The plateaus of the third and fourth spikes were also very small, indicating that there were some lingering effects of the AFPs, possibly due to binding of the AFPs to the cells.

These results lead to the conclusion that the AFPs block accumulation of Ca inside cells without interfering with other critical functions of the cell.

EXAMPLE 9

This example illustrates the use of AFGPs in protecting mammalian embryos subjected to hyperthermic, as opposed to hypothermic, conditions. The AFGPs were those of the Antarctic nototheniid fish (*Dissostichus mawsoni*), used in the physiological composition in which they occur in the fish, and the mammalian embryos were mouse embryos.

Mouse embryos at the two-cell stage were introduced in a T6 Whittingham medium containing 40 mg/mL AFGPs and held in the medium for 72 hours, without maintenance of an atmosphere of 5% $CO_2$ and without the temperature being controlled to 37° C. Further mouse embryos at the two-cell stage were introduced into a T6 Whittingham medium which did not contain AFGPs, and held in the same atmosphere for the same period of time as the first group. During this time, the concentration of $CO_2$ in the atmosphere above both media accidentally increased to about 8%, and the temperature rose to above 40° C. and remained at that high level through most of the time.

At the end of the 72-hour period, close to 80% of the mouse embryos in the AFGP-containing medium developed to the blastocyst stage, while less than 50% in the AFGP-free medium developed to the blastocyst stage. This demonstrates that the AFGPs are useful in protecting mammalian cells under non-optimal environmental conditions involving hyperthermic temperatures and a chemical environment which is incompatible with cell growth.

EXAMPLE 10

This example illustrates the use and effect of AFPs and AFGPs in combination with a conventional cryoprotectant in preservation solutions for the freezing of human red blood cells. Here it is shown that the AFPs and AFGPs when used at concentrations above a critical upper limit do physical damage to the cells by virtue of their effect on the formation of ice crystals, but that when used below that upper limit, the AFPs and AFGPs provide a beneficial effect by improving the cell survival rate over that achieved with the cryoprotectant alone.

In a first set of experiments, which is reported in Rubinsky, B., et al., *Cryobiology* 26(6):580 (1989), red blood cells were suspended in two preserving solutions. The first solution was physiological saline with 20% glycerol, and the second was physiological saline with 20% glycerol and 40 mg/mL AFGPs from Antarctic nototheniid fish (*Dissostichus mawsoni*). Each suspension was then frozen on a directional solidification apparatus, which is a moving-belt controlled-rate freezing apparatus disclosed in Rubinsky, B., U.S. Pat. No. 4,531,373, issued Jul. 30, 1985, and Rubinsky, B., et al., *Cryobiology* 22:55–68 (1985). The cooling rate was 1° C./min and was continued to a final temperature of −35° C., followed by thawing at 290° C./min. During cooling, the cells were observed and recorded by a video camera attached to a Zeiss Universal microscope with a magnification of 120× and 340×.

Upon freezing of the cells in the suspension which did not include the AFGPs, microscopic observation indicated that very large dendritic ice crystal structures formed which surrounded and entrapper the cells. When subsequently thawed, all cells in this suspension were free from injury, thus having survived the freezing process. By contrast, freezing of the suspension which did include the AFGPs resulted in the formation of small needle-like (spicular) ice crystals which pushed the cells forward, many of the cells becoming entrapped in unfrozen fluid channels between the crystals. As freezing continued, all of the entrapper cells that were frozen to −35° C. became distorted and sheared by the further growth of the spicular crystals. Upon thawing of the suspension, all of the cells which had been distorted by the spicular ice crystals were fragmented, and none of the cells survived.

These experiments demonstrate that the simple, straightforward addition of antifreeze proteins at physiological concentrations to solutions containing a cryoprotectant such as glycerol is detrimental, because of the well-known effect of the antifreeze proteins in forming spicular ice crystals. The ice crystals result in the complete destruction of cells and cause the cryoprotectant to lose its ability to preserve the cells.

A second set of experiments was performed, in which the preserving solution was a phosphate-buffered physiological solution with 20% glycerol, both alone and with 20 mg/mL AFPs (winter flounder), at a cooling rate of 25° C./min to a final temperature of −50° C., followed by thawing at a rate of 290° C./min. The viability of the cells after freezing and thawing was assessed by trypan blue exclusion and by visual (microscopic) observation of morphological intregrity. The cells in the preserving solution which did not contain the AFPs exhibited 60% viability, whereas those in the preserving solution which did contain the AFPs exhibited no viability, all cells having been destroyed. Video microscope recordings showed that the cells were destroyed by mechanical stress from the spicular ice crystals, similarly to the effects observed in the first set of experiments, in which AFGPs were used.

Since fresh red blood cells generally have a higher survival rate than aged red blood cells, a third set of experiments was performed, using red blood cells that had been aged by storage in phosphate-buffered physiological solution without glycerol for 14 days at 4° C. The cells were then divided into groups and suspended in each of various solutions containing glycerol and AFPs from winter flounder at various concentrations. Freezing was then performed at 25° C./min to −50° C., followed by thawing at 290° C./min, with microscopic observation recorded by video camera throughout the entire experiment. The results are shown in Table XI below, which includes observations of the presence or absence of ice spicules at the sub-freezing temperature and the survival rate upon thawing.

TABLE XI

Freezing of Aged Red Blood Cells With Glycerol Protection

| Suspension Solution | | Presence | |
|---|---|---|---|
| Glycerol Concentration | AFP Concentration | of Ice Spicules | Cell Survival Rate |
| 20% (weight) | 0 | no | 28% |
| 20% | 1 mg/mL | no | 52% |
| 20% | 6 mg/mL | partial | 27% |
| 20% | 9 mg/mL | partial | 19% |
| 20% | 20 mg/mL | yes | 0% |

The conclusion from this table is that the AFPs afford a beneficial effect to aged red blood cells when exposed to freezing conditions when used in a concentration range low enough to avoid spicular ice crystals that cause mechanical damage to the cells.

EXAMPLE 11

This example is a study of the freezing of tissue samples from rat liver, and offers a comparison of freezing behavior in the presence of AFGPs with freezing behavior in the absence of AFGPs, and a comparison of freezing behavior at a high cooling rate of 4000° C./minute with freezing behavior at a low cooling rate of 4° C./minute.

The AFGPs used in this study were isolated by ion exchange chromatography from Antarctic nototheniid (*Dissostichus mawsoni*), using one part by weight of combined fractions 1 through 5 with molecular weights 33,700 to 10,500, and three parts by weight of combined fractions 7 and 8 with molecular weights 3,500 and 2,600, respectively. The average molecular weight was approximately 4,000.

Adult female Sprague-Dawley rats, ages 45 to 50 days, were anesthetized with ether, and given a midline incision along the abdomen to expose the liver. The portal vein was then exposed and cannulated, and one thousand units of heparin were immediately injected into the vein. Selected rats were then injected with a 5-mL solution of physiological saline containing 200 mg (40 mg/mL) of AFGPs, and the vein was immediately clamped to prevent back flow. Within a period of 2 minutes, the livers were sectioned into rectangular samples, 8×4×3 mm in size, approximately 3 mm from the periphery of the lobe. The samples were segregated to distinguish those which had been perfused with AFGPs from those which had not, and placed lengthwise on No. 1 coverslips.

One coverslip containing both perfused and non-perfused samples was immediately plunged into a nitrogen slush maintained under vacuum at −213° C. No boiling was visible. The cooling rate of these samples in the slush was estimated at about 4000° C./min. A second coverslip containing both perfused and non-perfused samples was placed on the directional solidification apparatus of Example 10. On this apparatus, the samples were frozen at a controlled rate of 4° C./min from an initial temperature of 25° C. to a final temperature of −35° C. Freezing of these samples was accomplished in approximately 15 minutes. Immediately after freezing, the samples were immersed in a liquid nitrogen slush.

All samples were then placed in an AMRAY 1000 low-temperature scanning electron microscope (LTSEM). The samples were fractured in the cryochamber of the microscope to expose an area approximately 2 mm from the outer surface of the lobe. The samples were then gold-coated and transferred in a frozen hydrated state to the refrigerated stage of the LTSEM.

The following observations were made from photomicrographs obtained from the LTSEM at magnifications varying from 200× to 5000×.

- Samples Frozen at 4° C./min Without AFGPs: Expanded sinusoids (blood vessels) containing large, smooth, single continuous ice crystals were observed, and the hepatocytes surrounding the sinusoids were completely dehydrated and accordingly shrunken. These observations were previously reported by Rubinsky, B., et al., *Cryoletters* 8:370 (1987), and Rubinsky, B., et al., *Proc. Roy. Soc. Lond.* b234:343 (1988).
- Samples Frozen at 4000° C./min Without AFGPs: The normal structure of the hepatocytes was retained.
- Samples Frozen at 4° C./min With AFGPs: Submicron-size, needle-like ice crystals were observed in the blood vessels, in contrast to the large, smooth, single crystals observed in the samples which had been frozen at the same rate but not perfused with AFGPs. All crystals had the same orientation and all terminated at the blood vessel boundary. The hepatocytes retained the same intact appearance that was observed of the hepatocytes in the samples frozen at 4000° C./min without AFGPs. Note that in both cases, the hepatocytes were markedly distinguished in appearance from those of the samples frozen at 4° C. without AFGPs.
- Samples Frozen at 4000° C./min With AFGPs: Submicron-size, needle-like ice crystals were observed here as well, and again all had the same orientation and all terminated at the blood vessel boundary. The hepatocytes and cell nuclei were observed to be intact.

To summarize, the samples perfused with AFGPs and frozen at 4° C./min bore a closer resemblance to those which were frozen at 4000° C./min without AFGPs than to those which were frozen at 4° C./min without AFGPs, all observations of course having been made at the temperature of liquid nitrogen in the LTSEM. These results suggest that the AFGPs diffuse through the extracellular space, and interact with and protect the hepatocytes from the damaging effects of low temperatures. The results also confirm the ability of the AFGPs to aid in the preservation of mammalian tissue without the need for very fast cooling rates, and suggest the applicability of the AFGPs in the preservation of organs and foods.

Comparing these results with the results of Example 10 in which high concentrations of AFGPs were used in cell suspensions rather than tissue, one notices that, whereas the cells in the suspension suffered physical damage, those in the tissue did not. The distinction is related to the dense organization of cells in the tissue, and is attributable to the observation that in tissue the spicular ice crystals terminate at the blood vessel boundary.

EXAMPLE 12

This example illustrates the use of AFPs and AFGPs in the cryoprotection of mammalian cells during vitrification, demonstrating the protective effect of the these species on the cell membrane. The cells used in this example were immature pig oocytes, the AFPs were taken from winter flounder, sea raven, and ocean pout, and the AFGPs were taken from Antarctic nototheniid (*Dissostichus mawsoni*).

Immature pig oocytes were isolated from selected follicles of cyclic sows twenty minutes after slaughter at 20° C., according to a conventional procedure as described by Mattioli, M., et al., *Gamete Res.* 21:223-232 (1988). In preparation for low temperature exposure, the oocytes were first placed in one mL of PBS containing 0.1M sucrose and 20% FCS at 22° C. This was followed by a three-minute gradual mixing with one mL PBS containing 5% glycerol, 0.1M sucrose and 35% propylene glycol, according to a known procedure developed by Arav, A., et al., *Cryobiology* 66:567 (1988). The oocytes were transferred to slides containing 0.1 μL droplets of an apparent vitrification solution (AVS) consisting of the following:

| | |
|---|---|
| propylene glycol | 17.5% |
| glycerol | 2.5 |
| Fetal calf serum | 20.0 |
| Sucrose, 0.05M in PBS, supplemented with 0.4 m/v BSA, 0.34 mM pyruvate, 5.5 mM glucose, and 70 µg/mL kanamycin | Balance |

The solution was applied either alone or with AFPs or AFGPs at 20 mg/mL, one oocyte per droplet. Prior to cooling, the oocytes were placed on microscope slides in 0.1 µL droplets, and incubated on the slides for 6 minutes at 22° C. Cooling was then accomplished under microscope observation on the directional solidification apparatus of Example 10 at the rate of 1,700° C./min to −130° C. The slides were then held for fifteen minutes at −130° C., after which time the samples were warmed at the rate of 1,700° C./min to room temperature, all performed under microscope observation with a video camera. The microscope monitoring indicated that the droplets remained transparent in all experiments, indicating the absence of visible ice crystals. The monitoring further indicated that the morphology of the embryos and oocytes did not change during cooling and warming.

After warming, the oocytes were placed in 1 mL PBS with 20% FCS and 1M sucrose at room temperature for three minutes, followed by transfer to and equilibration in PBS containing 20% FCS for ten minutes at room temperature. The integrity of the oocytes was then evaluated by FDA staining and morphological examination focusing on the integrity of the oolemma. The technique used in this example was the same as that used in Example 1 above. Evaluations were also made on fresh oocytes prior to vitrification. The means and standard deviations of the FDA fluorescence intensity were calculated for each experiment.

The results are listed in Table XII, where the FDA intensity is expressed in a normalized form according to the equation:

$$I_n = \frac{(I - I_{AVS})}{(I_c - I_{AVS})}$$

where I represents the measured intensity, $I_n$ the normalized intensity, $I_{AVS}$ the intensity in AVS alone, and $I_c$ the intensity in the controls (fresh oocytes). The "Percent Intact" column gives the percentage of morphologically intact oocytes relative to the total oocytes in each sample. The criterion for morphological integrity was a smooth integral oolemma as opposed to a fragmented oolemma.

TABLE XII

Vitrification Tests on Pig Oocytes

| Preservation Medium | Normalized Fluorescence Intensity (%) | Percent Intact | No. of Oocytes |
|---|---|---|---|
| None (fresh oocytes) | 100 ± 1.2 | 100.0 | 43 |
| AVS | 0 ± 48.0 | 0.0 | 51 |
| AVS + 20 mg/mL AFGP (nototheniid) | 83.2 ± 20.0 | 58.6 | 29 |
| AVS + 20 mg/mL AFP I (winter flounder) | 78.2 ± 20.0 | 60.0 | 30 |
| AVS + 20 mg/mL AFP II (sea raven) | 74.3 ± 21.0 | 43.0 | 35 |
| AVS + 20 mg/mL AFP III (ocean pout) | 75.3 ± 11.5 | 37.5 | 32 |

The results in this table show that oocytes which were not protected by AFPs or AFGPs did not survive exposure to cryogenic temperatures. This is consistent with previous results in the literature, which show that pig oocytes are normally completely destroyed upon exposure to cryogenic temperatures. By contrast, where AFPs or AFPGs were included in the vitrification medium, protection against damage was demonstrated in each case, to roughly similar degrees, with significantly higher percent viability in each case, according to both the FDA and the morphological tests.

EXAMPLE 13

This example illustrates the use of AFPs and AFGPs in the cryoprotection of mouse embryos during vitrification. This example is reported in Rubinsky, B., et al., Cryobiology 29:69-79 (1992).

Mouse embryos at the two-cell stage were obtained from four-week-old C57B1/6J mice which were paired singly with CBA/CaJ males. The females were induced to superovulate by intraperitoneal injection of 5-7.5 I.U. PMSG (Sigma Chemical Company, St. Louis, Mo.), followed 48 hours later by 5-7.5 I.U. HCG (Sigma Chemical Company, St. Louis, Mo.). Forty hours after insemination, the oviducts were excised from the mice and the two-cell embryos flushed out and stored in PBS.

In preparation for low temperature exposure, the mouse embryos were placed in 1 mL of PBS and FCS, then combined with the apparent vitrificafion solution, all as described in Example 12. The embryos were then incubated on slides for 12 minutes at 4° C., followed by cooling to −130° C. at a rate of 1,700° C./min and warming at the same rate to room temperature, all conducted in the same manner as in Example 12, and with the same equipment.

Microscopic observation at a magnification of 340× indicated that the droplets remained transparent in all experiments, signifying the absence of visible ice crystals. Microscopic observation further confirmed that the morphology of the embryos and oocytes did not change during cooling and warming.

After warming, the mouse embryos were exposed for three minutes at 4° C. to 1 mL of PBS, with 20% FCS and 1 M sucrose, followed by transfer to and equilibration in PBS containing 20% FCS for 12 minutes at room temperature (22° C.). The embryos were then washed three times in T6 Whittingham medium cell culture medium, then cultured in the medium. After equilibration in the medium, the embryos were incubated at 37° C. under 5% $CO_2$ in air for 72 hours.

The viability of the mouse embryos after exposure to cryogenic temperatures was assessed by their ability to develop in vitro to the blastocyst stage while showing normal expanded morphology. The results of the viability tests are given in Table XIII, where the percent viability figures represent the number of embryos that reached the blastocyst stage as a percentage of the total number cooled. The control data here as in Example 12 represents tests where no cooling was done, the oocytes and embryos instead being held at room temperature.

TABLE XIII

Mouse Embryo Viability Tests

| Solution | Protocol | Viability |
|---|---|---|
| AVS | Control | 95% |
| AVS | Rapid cooling | 0% |
| AVS + 50 mg/mL AFP III (eel pout) | Rapid cooling | 0% |
| AVS + 40 mg/mL AFGP | Rapid cooling | 82.5% |
| AVS + 20 mg/mL AFGP | Rapid cooling | 80% |
| AVS + 10 mg/mL AFGP | Rapid cooling | 10% |
| AVS + 1 mg/mL AFGP | Rapid cooling | 0% |
| AVS + 1 mg/mL AFP I (winter flounder) | Rapid cooling | 10% (2/21) |
| AVS + 50 mg/mL AFP I (winter flounder) | Rapid cooling | 52% (11/21) |
| AVS + 1 mg/mL AFP III (ocean pout) | Rapid cooling | 35% (13/37) |
| AVS + 10 mg/mL AFP III (ocean pout) | Rapid cooling | 36% (14/39) |
| AVS + 20 mg/mL AFP III (ocean pout) | Rapid cooling | 62% (20/39) |
| AVS + 50 mg/mL AFP III (eel pout) | Rapid cooling | 74% (17/23) |

This data shows that with minor exceptions which are apparently attributable to deficiencies in the particular batches of AFPs used, both the AFPs and the AFGPs impart a beneficial effect to embryos undergoing vitrification by rapid cooling.

EXAMPLE 14

This example illustrates the use of AFPs and AFGPs in the cryoprotection of immature pig oocytes and pig embryos by vitrification in conjunction with a vitrification solution. A portion of this example is reported in Rubinsky, B., et al., *Cryoletters* 12:93–106 (1991).

The AFGPs used in this study were obtained from Antarctic nototheniid. The AFPs were obtained from the antarctic eel pout and had an average molecular weight of 6,900.

Immature pig oocytes were isolated from selected follicles of cyclic sows twenty minutes after slaughter at 20° C., according to a conventional procedure as described by Mattioli, et al., *Gamete Res.* 21:223–232 (1988). Two-cell stage pig embryos were collected from prepubertal gilts, average weight 90 kg. Estrus induction was carried out by administration of 1250 I.U. of PMSG (Sigma Chemical Company, St. Louis, Mo.), followed 56 hours later by administration of 750 I.U. of HCG (Sigma Chemical Company, St. Louis, Mo.). Two artificial inseminations were performed, one at 34 hours and the other at 46 hours after the HCG injection. The two-cell embryos were collected from the animal by mid-ventral laparoscopy under general anesthesia 60 hours after the HCG injection.

In preparation for low temperature exposure, the embryos and the oocytes were first placed in one mL of PBS containing 0.1M sucrose and 20% FCS at 22 ° C. This was followed by a three-minute gradual mixing with one mL PBS containing 5% glycerol, 0.1M sucrose and 35% propylene glycol, according to a known procedure developed by Arav, et al., *Cryobiology* 66:567 (1988). The embryos and oocytes were transferred to slides containing 0.1 μL droplets of an apparent vitrification solution (AVS) consisting of the following:

| propylene glycol | 17.5% |
|---|---|
| glycerol | 2.5 |

-continued

| Fetal calf serum | 20.0 |
|---|---|
| Sucrose, 0.05M in PBS, supplemented with 0.4 m/v BSA, 0.34 mM pyruvate, 5.5 mM glucose, and 70 μg/mL kanamycin | Balance |

The solution was applied either alone or with AFGP or AFP at either 40 mg/mL or 50 mg/mL, one embryo or oocyte per droplet. Prior to cooling, the oocytes and embryos were incubated on the slides for 6 minutes at 22 ° C.

Cooling was accomplished under microscope observation on the moving belt controlled-rate freezing apparatus of Example 10 at the rate of 1,700° C./min to −130° C. After fifteen minutes at −130° C., the samples were warmed at the rate of 1,700° C./min to room temperature. The microscope monitoring indicated that the droplets remained transparent in all experiments, indicating the absence of visible ice crystals. The monitoring further indicated that the morphology of the embryos and oocytes did not change during cooling and warming.

After warming, in preparation for viability assays in cell culture, the pig oocytes and pig embryos were placed for three minutes in 1 mL PBS, with 20% FCS and 1M sucrose at room temperature (22° C.), followed by transfer to and equilibration in PBS containing 20% FCS for 10 minutes at 22 ° C.

Prior to cell culture, all embryos and oocytes were washed three times in cell culture media. The pig oocytes were cultured in TCM-199 medium which was modified to contain 5 μg/mL of sheep luteinizing hormone (NIH S20), pig follicle stimulating hormone (LER 441-2) and 20 ng/mL of pig prolactin (LER 2073). The pig embryos were cultured in Brinster culture medium without glucose. After equilibration in cell culture medium, the oocytes and the embryos were incubated at 37° C. under 5% $CO_2$ in air, the pig oocytes for 44 hours, and the pig embryos for 24 hours.

The pig oocytes were fixed after 44 hours incubation in acetic acid/ethyl alcohol (1:3, volume basis) and stained with lacmoid stain. The viability of immature pig oocytes was assessed by their ability to develop from the germinal vesicular stage to the first metaphase (MI) or second metaphase (MII) stage in vitro, and to present a normal morphology (cytoplasmatic compactness, integrated oolemma, visible nuclear stage), using phase contrast microscopy as described by Mattioli, et al., *Gamete Res.* 21:223–232 (1988). The viability of the two-cell stage pig embryos was assessed by their ability to develop to the four-cell stage in culture, while maintaining integrated morphology (cell membrane and cytoplasm), using the same technique. The in vitro culture was stopped at the four-cell stage because early stage pig embryos often encounter the four-cell block when cultured in vitro and, therefore, further incubation would not be useful in assessing the viability of the embryos after exposure to cryogenic temperatures.

The results of the viability tests are presented in Table XIV below, in which the percent viability figures for the pig oocyte experiments represent the number of oocytes which reached either the MI or MII metaphase stage as a percent of the total number of immature oocytes cooled, and the percent viability figures for the pig embryos represent the number of embryos which reached the four-cell stage after in vitro development as a percent of the number of embryos cooled.

TABLE XIV

| Pig Oocyte and Embryo Viability Test Results | | |
|---|---|---|
| Solution | Protocol | Percent Viability |
| Pig Oocytes: | | |
| AVS | Control | 92 |
| AVS + 40 mg/mL AFGP | Control | 100 |
| AVS | Rapid cooling | 0 |
| AVS + 50 mg/mL AFP III | Rapid cooling | 0 |
| AVS + 40 mg/mL AFGP | Rapid cooling | 24.5 |
| Pig Embryos: | | |
| AVS | Control | 100 |
| AVS | Rapid cooling | 0 |
| AVS + 40 mg/mL AFGP | Rapid cooling | 26 |

The control data in Table XIV represent tests where no cooling was done, the oocytes and embryos instead being held at room temperature. The control tests with AVS alone indicate that the AVS had no adverse effect on either the oocytes or the embryos, whereas the control test on the oocytes with 40 mg/mL indicates that the AFGPs had no adverse effect, and in fact had a protective effect even without exposure to low temperatures. While the test on oocytes involving 50 mg/mL AFP did not show an improvement, all other tests showed viability upon culturing after the cooling/warming regime improved with the addition of AFGP. The test results with 50 mg/mL AFP were attributable to a poor batch of AFPs, and it will be noted that more favorable results are reported in Examples 12, 13 and 16. None of the oocytes and embryos equilibrated with AVS alone were viable when cultured after the cooling/warming regime.

This represents the first successful attempt to preserve pig embryos at temperatures below 10° C., and the fact that preservation was achieved at temperatures far below 0° C. is even more surprising. A review of the state of the art attesting to this fact is offered by Fahning, H. L., et al., *Cryobiology* 29(1): 1–19 (February, 1992).

Trypan blue exclusion and morphological examinations further indicated that in the tests involving rapid cooling and the use of AVS+40 mg/mL AFGP, the oolemma remained intact and the cell morphology was normal in 82% of the oocytes. In tests where AFGPs were not included, the cellular morphology appeared abnormal and the oolemma was disrupted in all oocytes, regardless of whether or not AVS was included in the suspension.

EXAMPLE 15

This example illustrates the use of AFPs in the protection of morulae and early blastocyst sheep embryos during exposure to hypothermic conditions (4° C.). The AFPs used in this study were isolated from winter flounder (AFP Type I) and ocean pout (AFP Type III). The compositions of the AFPs used in this study were the physiological compositions as they naturally occur in the fish from which they were isolated, purified from the fish blood plasma using Sephadex G75.

Sheep embryos at the morula and early blastocyst stages were obtained from ewes seven days after artificial insemination. The ewes were superovulated using p-FSH. The embryos were collected from the isolated fallopian tubes within twenty minutes after slaughter, using PBS. Only embryos of grades 1-2 were used.

Prior to the hypothermic exposure, the embryos were introduced into Eppendorf vials containing 0.5 mL of various preservation media, each consisting of PBS containing 1, 4 or 10 mg/mL of an additive, the additive being either BSA or one of the AFP compositions. The choice of 1 mg/mL and 10 mg/mL as concentrations for the AFPs was based on the results of Example 2. Control tests were performed without hypothermic exposure, using 4 mg/mL BSA in PBS.

The embryos were incubated in the various preservation media at 2-4° C. for four days. After this time period, the embryos were examined for viability according to three observations in in vitro culture—(1) the number of embryos which had developed to the expanded blastocyst stage, (2) the number of embryos which had hatched from the zona pellucida, and (3) the size of the hatched blastocytes after 72 hours of culture. The results of these observations are listed in Table XV below, which also includes the control data for comparison.

TABLE XV

| Hypothermic Preservation of Sheep Embryos | | | |
|---|---|---|---|
| Preservatin Medium | Percent Developed | Percent Hatched | Size (mm) |
| PBS + 1 mg/mL AFP III | 71% (15/21) | 57% (12/21) | 376 ± 24 |
| PBS + 10 mg/mL AFP III | 55% (11/20) | 45% (9/20) | 337 ± 3 |
| PBS + 1 mg/mL AFP I | 93% (14/15) | 73% (11/15) | 415 ± 125 |
| PBS + 10 mg/mL AFP I | 87% (13/15) | 60% (9/15) | 353 ± 137 |
| PBS + 4 mg/mL BSA | 60% (9/15) | 47% (7/15) | 260 ± 10 |
| PBS + 4 mg/mL BSA (without hypothermic exposure) | 86% (18/21) | 71% (15/21) | 453 ± 70 |

The data in Table XV show that of the embryos exposed to hypothermia in PBS with 4 mg/mL BSA, only 60% developed to the blastocyst stage, with a very low hatching rate and hatched blastocyte size compared to the control embryos which had not undergone hypothermic exposure. In contrast, in the presence of 1 mg/mL of AFP I (winter flounder), 93% of the embryos survived and displayed normal development, with a hatching rate and hatched blastocyte size substantially equal to those of the control.

These experiments confirm that the AFPs are an effective preservation medium for short term preservation and transportation of embryos. This compares favorably with conventional freezing methods, which commonly result in a loss of 40% to 50% of the embryos.

EXAMPLE 16

This example illustrates the use of AFPs and AFGPs in the cryoprotection of bovine embryos at the morula-blastocyst stage under vitrification conditions.

The AFGPs used in the this study were obtained from antarctic nototheniid fish. The AFPs were obtained from winter flounder (AFP Type I) and ocean pout (AFP Type III). All AFPs and AFGPs were purified from the fish blood plasma using Sephadex G75. Morula-early blastocyst embryos for use in this study were isolated from the fallopian tubes of superovulated cows, seven days after artificial insemination and thirty minutes after slaughter. Only embryos of grades 1-2 were used.

In preparation for the low-temperature exposure, the embryos were first placed in a preliminary solution consisting of one mL of PBS containing 0.4% BSA and 1.625M glycerol at 22 ° C. for sixteen minutes. The embryos were then transferred to droplets of a vitrification solution which consisted of PBS containing 4.875M glycerol (which will be referred to herein as "75% VS$_3$") supplemented with either BSA at 60 mg/mL or AFPs or AFGPs at 40 mg/mL. The droplets were then incubated on microscope slides at 22° C. for one minute.

Following the one-minute incubation, the slides containing the droplets were cooled on the moving-belt controlled-rate cooling apparatus of Example 10 at the rate of 4,992° C./minute to a final temperature of −120° C., and held at that temperature for fifteen minutes. The slides were then warmed at the rate of 4,992° C./minute to room temperature. During both cooling and warming, the slides were monitored through a microscope. The monitoring revealed that the droplets remained transparent in all experiments, indicating the absence of visible ice crystals. The monitoring further indicated that the morphology of the embryos did not change during either cooling or warming.

After warming, in preparation for the viability assays in cell culture medium, the embryos were placed in one mL PBS with 0.4% BSA and 1M sucrose at room temperature (22° C.) for ten minutes. This was followed by transfer to PBS containing 0.5M sucrose for 5 minutes, and then by a wash in PBS.

The embryos were then cultured in a culture medium for about one hour at 38° C. in 5% CO$_2$, then transferred to a synchronized recipient cow (day 7) at three embryos per cow. The pregnancy rate was then determined by ultrasound scanning. The results are shown in Table XVI below, in which the right column represents the percentage of pregnant cows relative to the total number of cows implanted with the embryos. The last entry in the table is a control test in which embryos were incubated in 60 mg/mL BSA in the 75% VS$_3$ without cooling, and thus without vitrification.

TABLE XVI

| Bovine Embryo Transfer Results Following Vitrification | |
|---|---|
| Preservation Medium | Percent Pregnancy |
| 75% VS$_3$ + 40 mg/mL AFP III | 33⅓% (⅓) |
| 75% VS$_3$ + 40 mg/mL AFP I | 75% (¾) |
| 75% VS$_3$ + 40 mg/mL AFGP | 50% (½) |
| 75% VS$_3$ + 60 mg/mL BSA | 0% |
| 75% VS$_3$ + 60 mg/mL BSA (without vitrification) | 66⅔% (⅔) |

These results demonstrate that AFPs and AFGPs can be used safely with vitrification procedures to produce the same pregnancy rate as in fresh control embryos.

The foregoing is offered primarily for purposes of illustration. It will be readily apparent to those skilled in the art that numerous variations, substitutions and modifications may be made in the materials used, the procedures followed and the situations and conditions to which the invention is applied without departing from the spirit and scope of the invention.

What is claimed is:

1. A method for the protection and preservation of the viability of mammalian cells undergoing exposure to a non-physiological temperature of up to about 40° C., said method comprising contacting said cells with a physiologically compatible liquid solution comprising one or more proteins having the molecular structure of thermal hysteresis proteins isolated and purified from a polar fish species.

2. A method in accordance with claim 1 in which said liquid solution is an aqueous solution.

3. A method in accordance with claim 1 in which said non-physiological temperature is at or below about 4° C., and said liquid solution is an aqueous solution.

4. A method in accordance with claim 1 in which said polar fish species is selected from the group consisting of Antarctic notothenioids, northern ocean gadoids, righteye flounders, cottids and eel pouts.

5. A method in accordance with claim 1 in which said one or more proteins have the molecular structure of thermal hysteresis proteins which are selected from the group consisting of:
   (a) antifreeze glycoproteins isolated and purified from a member selected from the group consisting of *Pagothenia borchgrevinki, Trematomus borchgrevinki, Dissostichus mawsoni, Gadus agac, Gadus morhua, Microgadus tomcod, Boreogadus saida* and *Eligenus gracilis;*
   (b) Type I antifreeze polypeptides isolated and purified from a member selected from the group consisting of *Pseudopleuronectus americanus, Limanda ferruginea, Myoxycephalus scorpius, Myoxycephalus aenaeus,* and *Myoxycephalus scorpiodes;*
   (c) Type II antifreeze polypeptides isolated and purified from a member selected from the group consisting of *Hemitripterus americanus, Osmerus mordex,* and *Clupea harengus harengus;* and
   (d) Type III antifreeze polypeptides isolated and purified from a member selected from the group consisting of *Macrozoarces americanus, Rhigophila dearborni* and *Lycodes polaris.*

6. A method in accordance with claim 1 in which said one or more proteins have the molecular structure of thermal hysteresis proteins which are selected from the group consisting of:
   (a) antifreeze glycoproteins isolated and purified from a member selected from the group consisting of *Pagothenia borchgrevinki, Trematomus borchgrevinki,* and *Dissostichus mawsoni;*
   (b) Type I antifreeze polypeptides isolated and purified from a member selected from the group consisting of *Pseudopleuronectus americanus* and *Limanda ferruginea;*
   (c) Type II antifreeze polypeptides isolated and purified from *Hemitripterus americanus;* and
   (d) Type III antifreeze polypeptides isolated and purified from a member selected from the group consisting of *Macrozoarces americanus, Rhigophila dearborni* and *Lycodes polaris.*

7. A method in accordance with claim 1 in which said one or more proteins have the molecular structure of thermal hysteresis proteins which are selected from the group consisting of:
   (a) antifreeze glycoproteins isolated and purified from *Dissostichus mawsoni;*
   (b) Type I antifreeze polypeptides isolated and purified from *Pseudopleuronectus americanus;*
   (c) Type II antifreeze polypeptides isolated and purified from *Hemitripterus americanus;* and
   (d) Type III antifreeze polypeptides isolated and purified from *Macrozoarces americanus.*

8. A method in accordance with claim 1 in which said liquid solution is an aqueous solution which further contains a tissue culture medium.

9. A method in accordance with claim 1 in which said mammalian cells are unconnected cells in an aqueous suspension.

10. A method in accordance with claim 9 in which said cells are human cells, said non-physiological temperature is a temperature substantially lower than human physiological temperature, and the total concentration of said one or more proteins in said aqueous solution is from about 0.1 mg/mL to about 40 mg/mL.

11. A method in accordance with claim 10 in which the total concentration of said one or more proteins in said aqueous solution is from about 0.1 mg/mL to about 3 mg/mL.

12. A method in accordance with claim 10 in which said cells are selected from the group consisting of human oocytes and human red blood cells, and the total concentration of said one or more proteins in said aqueous solution is from about 0.1 mg/mL to about 3 mg/mL.

13. A method for the protection and preservation of the viability of mammalian tissue undergoing exposure to a non-physiological temperature of up to about 40° C., said method comprising contacting said tissue with a physiologically compatible liquid solution comprising one or more proteins having the molecular structure of thermal hysteresis proteins isolated and purified from a polar fish species.

14. A method in accordance with claim 13 in which said method comprises perfusing said tissue with said liquid solution prior to exposure of said tissue to said non-physiological temperature and maintaining said tissue thus perfused throughout said exposure.

15. A method in accordance with claim 13 in which said mammalian tissue contains blood vessels and said method comprises perfusing said blood vessels with said liquid solution prior to exposure of said tissue to said non-physiological temperature and retaining said liquid solution in said blood vessels throughout said exposure.

16. A method in accordance with claim 13 in which the concentration of said proteins in said aqueous solution is from about 0.1 mg/mL to about 50 mg/mL.

17. A method in accordance with claim 13 in which said mammalian tissue is human tissue, and the concentration of said proteins in said aqueous solution is from about 0.1 mg/mL to about 3 mg/mL.

18. A method in accordance with claim 13 in which said liquid solution is an aqueous solution which further contains a tissue culture medium.

19. A method for the protection and preservation of the viability of a mammalian organ undergoing exposure to a non-physiological temperature of up to about 3° C. above physiological, said method comprising contacting said organ with a physiologically compatible liquid solution comprising one or more proteins having the molecular structure of thermal hysteresis proteins isolated and purified from a polar fish species.

20. A method in accordance with claim 19 in which said non-physiological temperature is a temperature substantially lower than the physiological temperature of said mammalian organ, and said method comprises perfusing blood vessels of said mammalian organ with said liquid solution prior to exposure of said mammalian organ to said non-physiological condition and retaining said liquid solution in said blood vessels throughout said exposure.

21. A method in accordance with claim 19 in which the concentration of said proteins in said aqueous solution is from about 0.1 mg/mL to about 50 mg/mL.

22. A method in accordance with claim 1 in which said exposure is performed under conditions in which said cells are not susceptible to the formation of ice crystals.

23. A method in accordance with claim 22 in which said non-physiological temperature is a temperature above the freezing temperature of water and below the physiological temperature of said cells.

24. A method in accordance with claim 23 in which the concentration of said proteins is from about 0.01 mg/mL to about 60 mg/mL.

25. A method in accordance with claim 23 in which the concentration of said proteins is from about 1 mg/mL to about 40 mg/mL.

26. A method in accordance with claim 22 in which said non-physiological temperature is a temperature at or below the glass formation temperature of said solution and said exposure is performed in the presence of a vitrifying agent which promotes vitrification in lieu of ice crystal formation.

27. A method in accordance with claim 26 in which said vitrifying agent contains one or more members selected from the group consisting of glycerol, dimethyl sulfoxide, ethylene glycol, polyvinylpyrrolidone, glucose, propanediol, and carboxymethyl cellulose.

28. A method in accordance with claim 26 in which the concentration of said proteins is from about 0.01 mg/mL to about 60 mg/mL.

29. A method in accordance with claim 26 in which the concentration of said proteins is from about 1 mg/mL to about 40 mg/mL.

30. A method in accordance with claim 1 in which said non-physiological temperature is a temperature at or below the freezing temperature of water and said exposure is performed in the presence of a non-peptide cryoprotectant.

31. A method in accordance with claim 30 in which said non-peptide cryoprotectant is one or more members selected from the group consisting of glycerol, dimethyl sulfoxide, ethylene glycol, polyvinylpyrrolidone, glucose, propanediol, and carboxymethyl cellulose.

32. A method in accordance with claim 30 in which said viable mammalian cells are unconnected cells in a cell suspension, said non-physiological temperature is a temperature substantially below the freezing temperature of water, said non-peptide cryoprotectant is present in an amount ranging from about 5% to about 35% by weight, and the total concentration of said one or more proteins is from about 0.1 mg/mL to about 3 mg/mL.

33. A method in accordance with claim 13 in which said non-physiological temperature is a temperature substantially below the freezing temperature of water, said non-peptide cryoprotectant is present in an amount ranging from about 5% to about 35% by weight, and the total concentration of said one or more is from about 0.1 mg/mL to about 60 mg/mL.

34. A method in accordance with claim 19 in which said non-physiological temperature is a temperature substantially below the freezing temperature of water, said non-peptide cryoprotectant is present in an amount ranging from about 5% to about 35% by weight, and the total concentration of said one or more proteins is from about 1 mg/mL to about 40 mg/mL.

35. A method of inhibiting the rate of ion transport across membranes of mammalian cells, said method comprising treating said membranes with an effective amount of one or more proteins having the molecular structure of thermal hysteresis proteins isolated and purified from a polar fish species.

36. A method in accordance with claim 35, said method comprising contacting said cell membranes with an aqueous solution of said one or more proteins having the molecular structure of thermal hysteresis proteins at a total protein concentration of at least about 0.01 mg/mL.

37. A method in accordance with claim 35, said method comprising contacting said cell membranes with an aqueous solution of said one or more proteins having the molecular structure of thermal hysteresis proteins at a total protein concentration of at least about 0.1 mg/mL.

38. A method in accordance with claim 35, said method comprising contacting said cell membranes with an aqueous solution of said one or more proteins having the molecular structure of thermal hysteresis proteins at a total protein concentration of from about 0.5 mg/mL to about 40 mg/mL.

* * * * *